United States Patent
Umemura et al.

(10) Patent No.: US 10,356,298 B2
(45) Date of Patent: Jul. 16, 2019

(54) BOARD INSPECTION APPARATUS

(71) Applicant: CKD Corporation, Aichi (JP)

(72) Inventors: Nobuyuki Umemura, Aichi (JP);
Akira Kato, Aichi (JP); Tsuyoshi Ohyama, Aichi (JP); Norihiko Sakaida, Aichi (JP)

(73) Assignee: CKD Corporation, Aichi (JP)

( * ) Notice: Subject to any disclaimer, the term of this patent is extended or adjusted under 35 U.S.C. 154(b) by 204 days.

(21) Appl. No.: 15/450,697

(22) Filed: Mar. 6, 2017

(65) Prior Publication Data

US 2017/0289416 A1 Oct. 5, 2017

(30) Foreign Application Priority Data

Mar. 29, 2016 (JP) .................. 2016-066092

(51) Int. Cl.
| | |
|---|---|
| *H04N 5/247* | (2006.01) |
| *H04N 5/225* | (2006.01) |
| *G01B 11/00* | (2006.01) |
| *G01N 21/956* | (2006.01) |
| *G06T 7/00* | (2017.01) |

(52) U.S. Cl.
CPC ......... *H04N 5/2256* (2013.01); *G01B 11/002* (2013.01); *G01N 21/956* (2013.01); *G06T 7/0004* (2013.01); *H04N 5/247* (2013.01); *G01N 2021/95638* (2013.01); *G01N 2201/061* (2013.01); *G06T 2207/30141* (2013.01)

(58) Field of Classification Search
CPC ... G01B 11/002; G01N 21/956; H04N 5/2256
USPC ............ 348/87, 92, 180; 382/145, 147, 143
See application file for complete search history.

(56) References Cited

U.S. PATENT DOCUMENTS

| | | | | |
|---|---|---|---|---|
| 5,293,217 A | * | 3/1994 | Sugawara | ............... G01N 21/88 250/559.08 |
| 6,290,382 B1 | * | 9/2001 | Bourn | ................ G01N 21/8806 362/294 |
| 2006/0165273 A1 | * | 7/2006 | Akiyama | ........... G01N 21/8901 382/145 |
| 2010/0074516 A1 | * | 3/2010 | Kawaragi | ............ G01N 21/956 382/149 |
| 2017/0276617 A1 | * | 9/2017 | Umemura | .......... G01N 21/9501 |

FOREIGN PATENT DOCUMENTS

JP      2006-184022 A     7/2006

* cited by examiner

*Primary Examiner* — Jefferey F Harold
*Assistant Examiner* — Jean W Desir
(74) *Attorney, Agent, or Firm* — Osha Liang LLP

(57) ABSTRACT

A board inspection apparatus is disclosed, which includes a surface-side irradiator irradiating a surface of each inspection area of a board, a surface-side camera taking a surface-side image of the surface, a rear face-side irradiator irradiating a rear face of each inspection area, a rear face-side camera taking a rear face-side image of the rear face, and a controller moving the surface-side irradiator and the surface-side camera to a position corresponding to the surface of each inspection area, moving the rear face-side irradiator and the rear face-side camera to a position corresponding to the rear face of each inspection area, and inspecting the surface and the rear face of each inspection area based on the surface-side image and the rear face-side image, respectively.

20 Claims, 11 Drawing Sheets

<PRIOR ART>

BOARD INSPECTION APPARATUS

BACKGROUND OF THE INVENTION

Technical Field

The present disclosure relates to a board inspection apparatus for inspecting both a surface and a rear face of a printed circuit board or the like.

Background Art

A printed circuit board with electronic components mounted on both a surface and a rear face thereof generally has electrode patterns formed on both a surface and a rear face of a base substrate that is formed from a glass epoxy resin, and resist films provided to protect these electrode patterns.

In a production line for mounting electronic components on such a printed circuit board, a procedure first prints solder paste at predetermined positions on both the surface and the rear face of the printed circuit board (solder printing process). The procedure subsequently applies an adhesive at the predetermined positions on both the surface and the rear face of the printed circuit board (adhesive applying process). The procedure subsequently mounts electronic components on both the surface and the rear face of the printed circuit board (mounting process). The electronic components are temporarily fastened by the viscosity of the solder paste or by means of the adhesive. The procedure then introduces the printed circuit board into a reflow furnace for soldering (reflow process).

For example, a board inspection apparatus configured to inspect the printing state of solder paste prior to mounting of components (solder printing inspection apparatus) or a board inspection apparatus configured to inspect a printed circuit board after mounting of components (mounting inspection apparatus) may be provided in this production line.

An inspection apparatus configured to simultaneously inspect both the surface and the rear face of the printed circuit board has conventionally been known as this board inspection apparatus.

In the board inspection apparatus configured to simultaneously inspect both the surface and the rear face, however, there is a possibility that part of light emitted toward one face side of the printed circuit board is transmitted through a hole pierced through the printed circuit board or through the glass epoxy resin of the base substrate and is leaked to the other face side of the printed circuit board. As a result, leakage of light from one face side is likely to affect and decrease the inspection accuracy with regard to inspection of the other face side of the printed circuit board.

In order to reduce such a problem, a recently proposed inspection apparatus places illumination units at offset positions on the surface side and on the rear face side of the printed circuit board or performs an inspection simultaneously with regard to both the surface side and the rear face side of the printed circuit board that are irradiated with the light of the same color (as described in, for example, Patent Literature 1).

CITATION LIST

Patent Literature

PTL 1: JP 2006-184022A

SUMMARY OF THE INVENTION

Even in the configuration of Patent Literature 1 described above, however, simultaneous light emission on both the surface side and the rear face side of the printed circuit board is likely to cause a slight leakage of light to the opposite side. There are thus still concerns about the effect on the inspection accuracy.

For example, in a configuration that performs three-dimensional measurement (inspection) based on a difference between luminance values of a plurality of image data taken with patterned light having different phases, for example, three-dimensional measurement by the phase shift method, even a slight leakage of even the light of the same color from the other face side of the printed circuit board is likely to provide a significant effect on the inspection accuracy with regard to inspection of one face side of the printed circuit board.

A configuration that performs, for example, inspection of the rear face side of the printed circuit board after completion of inspection of the surface side of the printed circuit board is, on the other hand, likely to increase the inspection time.

For example, when a large number of inspection areas are set on each of the surface and the rear face of the printed circuit board, the inspection time is likely to be increased significantly (as shown in FIG. 9).

A board inspection apparatus according to one or more embodiments improve the inspection accuracy and increase the inspection speed with regard to double-sided inspection of a board.

The following describes each of various aspects of the invention. Functions and advantageous effects that are characteristic of each of the aspects are also described as appropriate.

Aspect 1: There is provided a board inspection apparatus configured to perform an inspection with regard to both a surface and a rear face of a board. The board inspection apparatus comprises at least one surface-side irradiator configured to irradiate a predetermined inspection area on a surface side of the board with predetermined light; a surface-side imaging unit configured to take an image of the predetermined inspection area on the surface side of the board that is irradiated with the predetermined light; a surface-side moving unit configured to move the surface-side irradiator and the surface-side imaging unit to a position corresponding to the predetermined inspection area on the surface side of the board; at least one rear face-side irradiator configured to irradiate a predetermined inspection area on a rear face side of the board with predetermined light; a rear face-side imaging unit configured to take an image of the predetermined inspection area on the rear face side of the board that is irradiated with the predetermined light; a rear face-side moving unit configured to move the rear face-side irradiator and the rear face-side imaging unit to a position corresponding to the predetermined inspection area on the rear face side of the board; and an inspection unit configured to perform an inspection with regard to the predetermined inspection area on the surface side of the board, based on at least one image data obtained by an image acquisition process with regard to the predetermined inspection area on the surface side of the board performed by the surface-side irradiator and the surface-side imaging unit, and configured to perform an inspection with regard to the predetermined inspection area on the rear face side of the board, based on at least one image data obtained by an image acquisition process with regard to the predetermined inspection area on the rear face side of the board performed by the rear face-side irradiator and the rear face-side imaging unit. The image acquisition process with regard to one inspection area among a plurality of inspection areas set on the surface side of the board and the image acquisition process with regard to one inspection area among a plurality of inspection areas set on the rear face side of the board are alternately performed by: causing the image acquisition process (at least one imaging process) with regard to one inspection area among the plurality of inspection areas set on the surface side of the board to be performed by the surface-side irradiator and the surface-side imaging unit, while stopping emission of light from the rear face-side irradiator, and subsequently moving the surface-side irradiator and the surface-side imaging unit to a position corresponding to a next inspection area and causing the image acquisition process (at least one imaging process) with regard to one inspection area among the plurality of inspection areas set on the rear face side of the board to be performed by the rear face-side irradiator and the rear face-side imaging unit, while stopping emission of light from the surface-side irradiator; and causing the image acquisition process (at least one imaging process) with regard to one inspection area among the plurality of inspection areas set on the rear face side of the board to be performed by the rear face-side irradiator and the rear face-side imaging unit, while stopping emission of light from the surface-side irradiator, and subsequently moving the rear face-side irradiator and the rear face-side imaging unit to a position corresponding to a next inspection area and causing the image acquisition process (at least one imaging process) with regard to one inspection area among the plurality of inspection areas set on the surface side of the board to be performed by the surface-side irradiator and the surface-side imaging unit, while stopping emission of light from the rear face-side irradiator.

The configuration that enables the irradiator and the imaging unit with regard to the surface side of the board and the irradiator and the imaging unit with regard to the rear face side of the board to be separately driven and controlled like the aspect 1 described above is likely to cause the inspection periods of the surface and the rear face of the board to be overlapped, while enhancing the efficiency of inspection.

The configuration of the above aspect 1, however, moves the irradiator and the imaging unit with regard to the surface side (or the rear face side) to a position corresponding to a next inspection area and performs the image acquisition process with regard to the rear face side (or the surface side) of the board, after performing the image acquisition process with regard to the surface side (or the rear face side) of the board.

This configuration thus alternately repeats the image acquisition process with regard to the surface side of the board and the image acquisition process with regard to the rear face side of the board, so as to perform the image acquisition processes with regard to the plurality of inspection areas on the surface side of the board and the image acquisition processes with regard to the plurality of inspection areas on the rear face side of the board at the same time.

This configuration accordingly increases the inspection speed with regard to double-sided inspection of the board, compared with a configuration that performs, for example, all the image acquisition processes with regard to the plurality of inspection areas on the rear face side of the board after completion of all the image acquisition processes with regard to the plurality of inspection areas on the surface side of the board.

The configuration of this aspect stops emission of light on the rear face side (or on the surface side) during an image acquisition period with regard to the surface side (or with regard to the rear face side) of the board. This configuration enables image data of the high accuracy to be obtained without causing leakage of light to the surface side (or to the rear face side). As a result, this configuration improves the inspection accuracy with regard to double-sided inspection of the board.

As a result, this improves the inspection accuracy and increases the inspection speed with regard to double-sided inspection of the board.

Aspect 2: In the board inspection apparatus described in the above aspect 1, the image acquisition process by the rear face-side irradiator and the rear face-side imaging unit may be performed (completed) during a moving time period of the surface-side irradiator and the surface-side imaging unit, and the image acquisition process by the surface-side irradiator and the surface-side imaging unit may be performed (completed) during a moving time period of the rear face-side irradiator and the rear face-side imaging unit.

The configuration of the above aspect 2 utilizes the moving time period in which the irradiator and the imaging unit for one side (for example, the surface-side irradiator and the surface-side imaging unit) are moved to a position corresponding to a next inspection area to perform an image acquisition process by the irradiator and the imaging unit for the other side (for example, the rear face-side irradiator and the rear face-side imaging unit).

This configuration enables all image acquisition processes with regard to a plurality of inspection areas on the entire rear face side (or on the entire surface side) of the board to be performed without extending the minimum time period required for completion of all image acquisition processes with regard to a plurality of inspection areas on the entire surface side (or on the entire rear face side) of the board (including moving time periods between the image acquisition processes). As a result, this increases the inspection speed with regard to double-sided inspection of the board.

Aspect 3: In the board inspection apparatus described in either the above aspect 1 or the above aspect 2, the surface-side irradiator and the surface-side imaging unit may be sequentially moved to positions corresponding to the plurality of inspection areas set on the surface side of the board according to a predetermined sequence of inspection, and the image acquisition processes with regard to the plurality of inspection areas may be performed sequentially. The rear face-side irradiator and the rear face-side imaging unit may be sequentially moved to positions corresponding to the plurality of inspection areas set on the rear face side of the board according to a predetermined sequence of inspection, and the image acquisition processes with regard to the plurality of inspection areas may be performed sequentially. The sequence of inspection with regard to the surface side of the board may be set such that a moving path of the surface-side irradiator and the surface-side imaging unit is a shortest path from a predetermined starting point, and/or the sequence of inspection with regard to the rear face side of the board may be set such that a moving path of the rear face-side irradiator and the rear face-side imaging unit is a shortest path from a predetermined starting point.

The configuration of the above aspect 3 sets the sequence of inspection such that the moving path of the irradiator and the imaging unit is the shortest path from the predetermined starting point (for example, a predetermined inspection area or a recognition mark imaged last) with respect to at least one of the surface side and the rear face side of the board. This further increases the speed of inspection.

Aspect 4: In the board inspection apparatus described in any of the above aspects 1 to 3, at least one specified object for positioning (for example, a recognition mark or a through hole) may be provided on the surface of the board, and at least one specified object for positioning (for example, a recognition mark or a through hole) may be provided on the rear face of the board. With regard to the surface side of the board, after the at least one specified object is individually imaged by the surface-side imaging unit, the image acquisition processes with regard to the plurality of inspection areas set on the surface side of the board may be sequentially performed. With regard to the rear face side of the board, after the at least one specified object is individually imaged by the rear face-side imaging unit, the image acquisition processes with regard to the plurality of inspection areas set on the rear face side of the board may be sequentially performed.

The configuration of the above aspect 4 takes an image of the specified object and performs positioning. This further improves the inspection accuracy with regard to double-sided inspection of the board.

For example, the configuration of the board inspection apparatus may comprise:

"a surface-side corrector configured to correct a relative positional relationship between the surface-side imaging unit and the surface of the board, based on position information of a plurality of the specified objects that are imaged by the surface-side imaging unit on the surface side of the board; and a rear face-side corrector configured to correct a relative positional relationship between the rear face-side imaging unit and the rear face of the board, based on position information of a plurality of the specified objects that are imaged by the rear face-side imaging unit on the rear face side of the board".

Aspect 5: In the board inspection apparatus described in the above aspect 4, with regard to at least one of the surface side and the rear face side of the board, an inspection area in a shortest distance from a specified object that is imaged last out of the at least one specified object may be set as an inspection area for which the image acquisition process is to be performed first.

The configuration of the above aspect 5 starts inspection from an inspection area that is located nearest to the specified object that is imaged last out of the at least one specified object. This shortens the time period elapsed until a start of inspection in the first inspection area and thereby increases the speed of inspection.

Aspect 6: The board inspection apparatus described in either the above aspect 4 or the above aspect 5 may further comprise a storage unit configured to store a relative positional relationship between the surface-side imaging unit and the rear face-side imaging unit (and a relative positional relationship between the surface and the rear face of the board) obtained in advance; and a corrector configured to correct a relative positional relationship between the surface-side imaging unit and the surface of the board and a relative positional relationship between the rear face-side imaging unit and the rear face of the board, based on position information of one specified object on the surface side of the board that is imaged by the surface-side imaging unit, position information of one specified object on the rear face side of the board that is imaged by the rear face-side imaging unit, and the relative positional relationship between the surface-side imaging unit and the rear face-side imaging unit (and the relative positional relationship between the surface and the rear face of the board) stored in the storage unit.

The configuration of the above aspect 6 uses the position information of the specified object with regard to one face out of the surface and the rear face of the board as the position information with regard to the other face and thereby allows for the correction of positions by taking an image of only one specified object (i.e., without taking images of a plurality of specified objects) on each of the surface and the rear face of the board. This further improves the inspection accuracy with respect to double-sided inspection of the board.

This configuration starts inspection without taking images of a plurality of specified objects on each of the surface and the rear face of the board and thereby increases the speed of inspection.

For example, this configuration may perform the correction described above, based on the relative positional relationship between the surface-side imaging unit and the rear face-side imaging unit determined in advance by calibration or the like (for example, offset amounts of both the imaging units), on the assumption that there is no positional misalignment (for example, stacking deviation or misalignment of patterns) between the surface and the rear face of the board.

When there is a positional misalignment between the surface and the rear face of the board, the correction described above may be performed, for example, by obtaining in advance information on the positional misalignment between the surface and the rear face of the board (i.e., relative positional relationship between the surface and the rear face of the board) detected in a previous process (for example, pattern inspection process).

For example, a through hole formed to pass through the board between the surface and the rear face may be used as the specified object for positioning. This allows for the above correction without taking into account the positional misalignment between the surface and the rear face of the board.

Aspect 7: In the board inspection apparatus described in any one of the above aspects 1 to 6, at least one of the surface-side irradiator and the rear face-side irradiator may be configured to emit patterned light having a light intensity distribution of a stripe shape as the predetermined light. The inspection unit may be configured to perform three-dimensional measurement by a phase shift method, based on a plurality of image data taken with the patterned light of different phases.

In the case of three-dimensional measurement by the phase shift method, as described above, even a slight leakage of light from the other face side of the board is likely to provide a significant effect on the inspection accuracy with regard to inspection of one face side of the board.

The three-dimensional measurement by the phase shift method requires imaging one inspection area multiple times. Accordingly a configuration of performing all image acquisition processes with regard to a plurality of inspection areas on the rear face side of the board after completion of all image acquisition processes with regard to a plurality of inspection areas on the surface side of the board is likely to remarkably increase the inspection time.

The configuration of the above aspect 7 accordingly ensures the better functions and the better effects achieved by the configuration of the above aspect 1. This improves the inspection accuracy and increases the inspection speed with regard to double-sided inspection of the board.

Aspect 8: In the board inspection apparatus described in any one of the above aspects 1 to 7, the board may be either a printed circuit board on which solder paste is printed or a wafer substrate on which a solder bump is formed.

The configuration of the above aspect 8 serves to perform an inspection for solder paste printed on the printed circuit board or an inspection for a solder bump formed on the wafer substrate. Accordingly the functions and the advantageous effects of each of the above aspects may be provided in inspection of solder paste or in inspection of solder bumps. This allows for quality determination of solder printing or solder bump formation with the high accuracy. As a result, this configuration improves the inspection accuracy and increases the inspection speed with regard to inspection of solder printing or with regard to inspection of solder bumps.

DETAILED DESCRIPTION

First Embodiment

The following describes one embodiment with reference to the drawings. First, the configuration of a printed circuit board as an inspection object is described in detail. According to this embodiment, the inspection object is a double-layer board (double-sided board) having electronic components mounted on both a surface and a rear face thereof.

Figure 2:
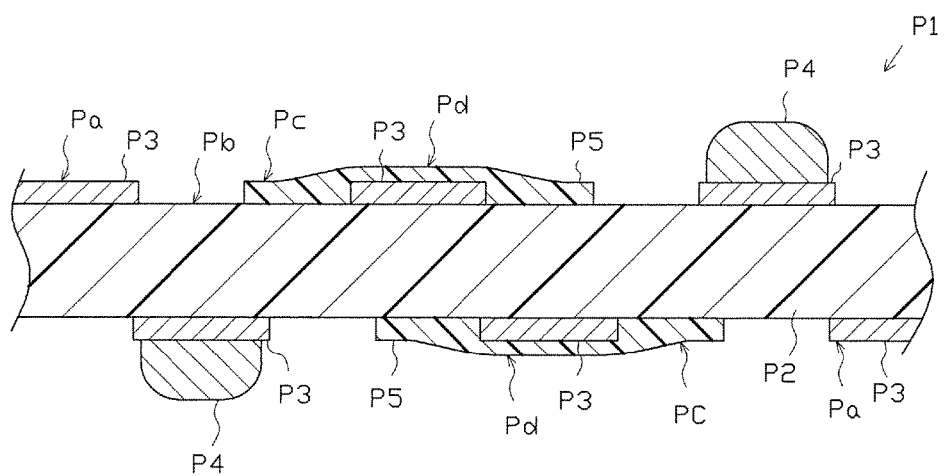
FIG. 2 is a partly enlarged sectional view illustrating a printed circuit board according to one or more embodiments of the invention.

As shown in FIG. 2, a printed circuit board P1 has electrode patterns P3 that are formed from a copper foil and are provided on both a surface and a rear face of a base substrate P2 that is a flat plate type and is formed from, for example, a glass epoxy resin. Additionally, solder paste P4 that is a measurement object is printed and formed on specific regions (for example, lands and pads) of the electrode patterns P3. An area in which the solder paste P4 is printed is called "solder printed area". A remaining part other than the solder printed area is generally called "background area". This background area includes an area in which the electrode pattern P3 is exposed (shown by a reference sign Pa), an area in which the base substrate P2 is exposed (shown by a reference sign Pb), an area in which the base substrate P2 is coated with a resist film P5 (shown by a reference sign Pc), and an area in which the electrode pattern P3 is coated with the resist film P5 (shown by a reference sign Pd). Both the surface and the rear face of the printed circuit board P1 are coated with the resist film P5, in order to prevent the solder paste P4 from adhering to any remaining part other than a specified wiring area.

Figure 6:
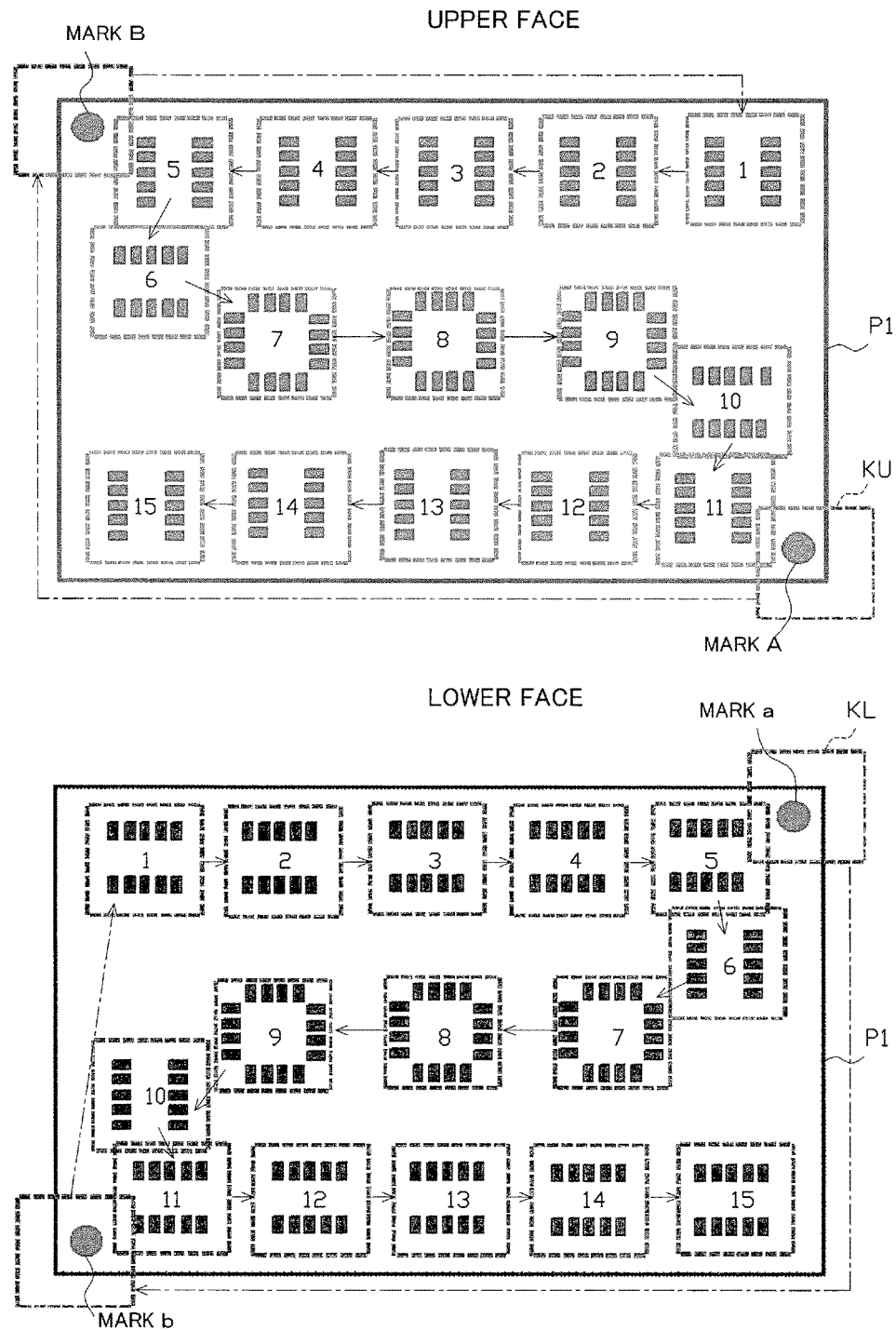
FIG. 6 is a diagram illustrating sequences of inspection on the upper face side and on the lower face side of the printed circuit board according to one or more embodiments of the invention.

Recognition marks are provided as specified objects for positioning on both the surface and the rear face of the printed circuit board P1 (as shown in, for example, FIG. 6). More specifically, a first recognition mark [A] and a second recognition mark [B] are provided respectively at two corners arranged on a predetermined diagonal line among four corners on the surface side of the printed circuit board P1. Similarly, a first recognition mark [a] and a second recognition mark [b] are provided respectively at two corners arranged on a predetermined diagonal line among four corners on the rear face side of the printed circuit board P1.

Figure 1:
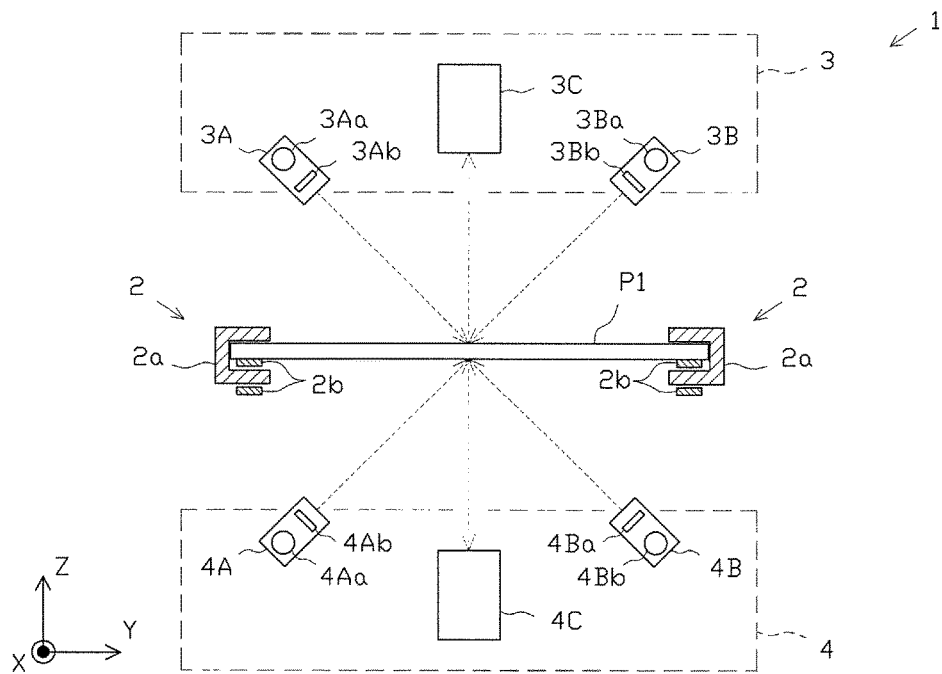
FIG. 1 is a schematic configuration diagram schematically illustrating a board inspection apparatus according to one or more embodiments of the invention.

Next, the configuration of a board inspection apparatus 1 configured to perform an inspection of the printed circuit board P1 is described below in detail. The board inspection apparatus 1 according to this embodiment is used as a solder printing inspection apparatus configured to perform an inspection for the printing state of the solder paste P4 at a stage prior to mounting of electronic components. FIG. 1 is a schematic configuration diagram schematically illustrating the board inspection apparatus 1.

As shown in FIG. 1, the board inspection apparatus 1 includes a conveying mechanism 2 configured to, for example, convey and position the printed circuit board P1, an upper face inspection unit 3 configured to perform an inspection with regard to an the upper face (surface) side of the printed circuit board P1, a lower face inspection unit 4 configured to perform an inspection with regard to a lower face (rear face) side of the printed circuit board P1, and a control device 6 (shown in FIG. 3) configured to perform various controls, image processing and arithmetic processing in the board inspection apparatus 1, for example, drive control of the conveying mechanism 2 and both the inspection units 3 and 4. According to this embodiment, the control device 6 serves as the inspection unit.

The conveying mechanism 2 includes a pair of conveying rails 2a arranged along a conveying direction of the printed circuit board P1, endless conveyor belts 2b provided to be rotatable relative to the respective conveying rails 2a, drive means (not shown) such as motors configured to drive the respective conveyor belts 2b, and a chuck mechanism (not shown) configured to locate the printed circuit board P1 at a predetermined position. The conveying mechanism 2 is driven and controlled by the control device 6.

The above configuration causes the printed circuit board P1 carried into the board inspection apparatus 1 to be placed on the conveyor belts 2b, while respective side edges of the printed circuit board P1 in a width direction that is perpendicular to the conveying direction are inserted into the respective conveying rails 2a. The conveyor belts 2b subsequently start operation to convey the printed circuit board P1 to a predetermined inspection position. When the printed circuit board P1 reaches the inspection position, the conveyor belts 2b are stopped and the chuck mechanism is operated. The conveyor belts 2b are pressed up by the operation of this chuck mechanism, so that the respective side edges of the printed circuit board P1 are placed between the conveyor belts 2b and the upper side portions of the conveying rails 2a. This causes the printed circuit board P1 to be located and fixed at the inspection position. After termination of inspection, the fixation by the chuck mechanism is released, and the conveyor belts 2b start operation. This causes the printed circuit board P1 to be carried out of the board inspection apparatus 1. The configuration of the conveying mechanism 2 is naturally not limited to the configuration of this embodiment described above, but any other configuration may be employed for the conveying mechanism 2.

The upper face inspection unit 3 is provided above the conveying rails 2a (i.e., the conveying path of the printed circuit board P1). The lower face inspection unit 4 is provided below the conveying rails 2a (i.e., the conveying path of the printed circuit board P1).

The upper face inspection unit 3 includes a first upper face inspection illumination device 3A and a second upper face inspection illumination device 3B provided as the surface-side irradiator configured to irradiate a predetermined inspection area on the upper face of the printed circuit board P1 with a predetermined stripe pattern for three-dimensional measurement emitted obliquely downward (patterned light having a stripe-shaped light intensity distribution), an upper face inspection camera 3C provided as the surface-side imaging unit configured to take an image of the predetermined inspection area on the upper face of the printed circuit board P1 from immediately above the predetermined inspection area, an X-axis moving mechanism 3D (shown in FIG. 3) configured to allow for the move in an X-axis direction, and a Y-axis moving mechanism 3E (shown in FIG. 3) configured to allow for the move in a Y-axis direction. The upper face inspection unit 3 is driven and controlled by the control device 6.

The "inspection area" on the upper face of the printed circuit board P1 denotes one area among a plurality of areas set in advance on the upper face (surface) of the printed circuit board P1, based on the size of an imaging view (imaging range) KU of the upper face inspection camera 3C specified as one unit (as shown in the upper drawing of FIG. 6).

The control device 6 drives and controls the X-axis moving mechanism 3D and the Y-axis moving mechanism 3E, so as to move the upper face inspection unit 3 (imaging view KU) to a position above an arbitrary inspection area on the upper face of the printed circuit board P1 that is located and fixed at the inspection position. The upper face inspection unit 3 is successively moved to each of a plurality of inspection areas set on the upper face of the printed circuit board P1 and performs an inspection with regard to each inspection area. This configuration performs an inspection for the entire upper face of the printed circuit board P1 (as shown in the upper drawing of FIG. 6). The X-axis moving mechanism 3D and the Y-axis moving mechanism 3E accordingly constitute the surface-side moving unit according to the embodiment.

The first upper face inspection illumination device 3A includes a light source 3Aa configured to emit predetermined light and a grid plate 3Ab configured to convert the light emitted from the light source 3Aa into a stripe pattern. The first upper face inspection illumination device 3A is driven and controlled by the control device 6. The light emitted from the light source 3Aa is introduced to a condenser lens (not shown) to be converted into parallel light and is subsequently introduced via the grid plate 3Ab to a projection lens (not shown) to be projected as a stripe pattern onto the printed circuit board P1.

The grid plate 3Ab has such a configuration that linear translucent portions that allow for transmission of light and linear light shielding portions that intercept light are arranged alternately in a predetermined direction perpendicular to the optical axis of the light source 3Aa. This configuration enables a stripe pattern having a light intensity distribution in a square wave form or in a trapezoidal wave form to be projected onto the printed circuit board P1. According to this embodiment, the direction of stripes in the projected stripe pattern is parallel to the X-axis direction and is perpendicular to the Y-axis direction.

The stripe pattern may not be in a perfect square wave form, since the light passing through the grid plate 3Ab is generally not the perfectly parallel light and a halftone range is likely to arise on a boundary between a "bright area" and a "dark area" of the stripe pattern, due to the diffraction effect or the like on a boundary between the light translucent portion and the light shielding portion.

A steep luminance slope of the halftone range on the boundary between the "bright area" and the "dark area" provides a stripe pattern having a light intensity distribution in a square wave form. A gentle luminance slope of the halftone range, on the other hand, provides a stripe pattern having a light intensity distribution in a trapezoidal wave form. This may, however, depend on the configuration of the grid plate 3Ab, for example, the intervals of the arrangement of the light translucent portions and the light shielding portions.

Additionally, the first upper face inspection illumination device 3A includes drive means (not shown) such as a motor provided to move the grid plate 3Ab. The control device 6 drives and controls this drive means, so as to continuously move the grid plate 3Ab at a constant speed in the predetermined direction perpendicular to the optical axis of the light source 3Aa. This enables the stripe pattern to be projected on the printed circuit board P1 such as to be shifted along the Y-axis direction.

The second upper face inspection illumination device 3B includes a light source 3Ba configured to emit predetermined light and a grid plate 3Bb configured to convert the light emitted from the light source 3Ba into a stripe pattern. The second upper face inspection illumination device 3B is driven and controlled by the control device 6. The configuration of the second upper face inspection illumination device 3B (for example, the configuration involved in the light source 3Ba and the grid plate 3Bb) is similar to the configuration of the first upper face inspection illumination device 3A described above, so that its detailed description is omitted.

The upper face inspection camera 3C includes, for example, a lens and an imaging element. According to this embodiment, a CCD sensor is employed as the imaging element.

The upper face inspection camera 3C is driven and controlled by the control device 6. For example, the control device 6 performs an imaging process using the upper face inspection camera 3C in synchronism with the moving process of the grid plate 3Ab or 3Bb, in response to a signal from an encoder (not shown) provided in the drive means of the grid plate 3Ab or 3Bb.

Image data taken by the upper face inspection camera 3C is converted into a digital signal in the upper face inspection camera 3C, is transferred in the form of the digital signal to the control device 6, and is stored into an image data storage unit 24 described later. The control device 6 performs, for example, image processing and arithmetic processing as described later, based on the image data.

Like the upper face inspection unit 3 described above, the lower face inspection unit 4 includes a first lower face inspection illumination device 4A and a second lower face inspection illumination device 4B provided as the rear face-side irradiator configured to irradiate a predetermined inspection area on the lower face of the printed circuit board P1 with a predetermined stripe pattern for three-dimensional measurement emitted obliquely upward (patterned light having a stripe-shaped light intensity distribution), a lower face inspection camera 4C provided as the rear face-side imaging unit configured to take an image of the predetermined inspection area on the lower face of the printed circuit board P1 from immediately below the predetermined inspection area, an X-axis moving mechanism 4D (shown in FIG. 3) configured to allow for the move in the X-axis direction, and a Y-axis moving mechanism 4E (shown in FIG. 3) configured to allow for the move in the Y-axis direction. The lower face inspection unit 4 is driven and controlled by the control device 6.

The "inspection area" on the lower face of the printed circuit board P1 denotes one area among a plurality of areas set in advance on the lower face (rear face) of the printed circuit board P1, based on the size of an imaging view (imaging range) KL of the lower face inspection camera 4C specified as one unit (as shown in the lower drawing of FIG. 6).

The control device 6 drives and controls the X-axis moving mechanism 4D and the Y-axis moving mechanism 4E, so as to move the lower face inspection unit 4 (imaging view KL) to a position below an arbitrary inspection area on the lower face of the printed circuit board P1 that is located and fixed at the inspection position. The lower face inspection unit 4 is successively moved to each of a plurality of inspection areas set on the lower face of the printed circuit board P1 and performs an inspection with regard to each inspection area. This configuration performs an inspection for the entire lower face of the printed circuit board P1 (as shown in the lower drawing of FIG. 6). The X-axis moving mechanism 4D and the Y-axis moving mechanism 4E accordingly constitute the rear face-side moving unit according to the embodiment.

The first lower face inspection illumination device 4A includes a light source 4Aa configured to emit predetermined light and a grid plate 4Ab configured to convert the light emitted from the light source 4Aa into a stripe pattern. The first lower face inspection illumination device 4A is driven and controlled by the control device 6. The configuration of the first lower face inspection illumination device 4A (for example, the configuration involved in the light source 4Aa and the grid plate 4Ab) is similar to the configuration of the first upper face inspection illumination device 3A described above, so that its detailed description is omitted.

The second lower face inspection illumination device 4B includes a light source 4Ba configured to emit predetermined light and a grid plate 4Bb configured to convert the light emitted from the light source 4Ba into a stripe pattern. The second lower face inspection illumination device 4B is driven and controlled by the control device 6. The configuration of the second lower face inspection illumination device 4B (for example, the configuration involved in the light source 4Ba and the grid plate 4Bb) is similar to the configuration of the first upper face inspection illumination device 3A described above, so that its detailed description is omitted.

The lower face inspection camera 4C includes, for example, a lens and an imaging element. According to this embodiment, a CCD sensor is employed as the imaging element. The configuration of the lower face inspection camera 4C is similar to the configuration of the upper face inspection camera 3C described above, so that its detailed description is omitted.

Figure 3:
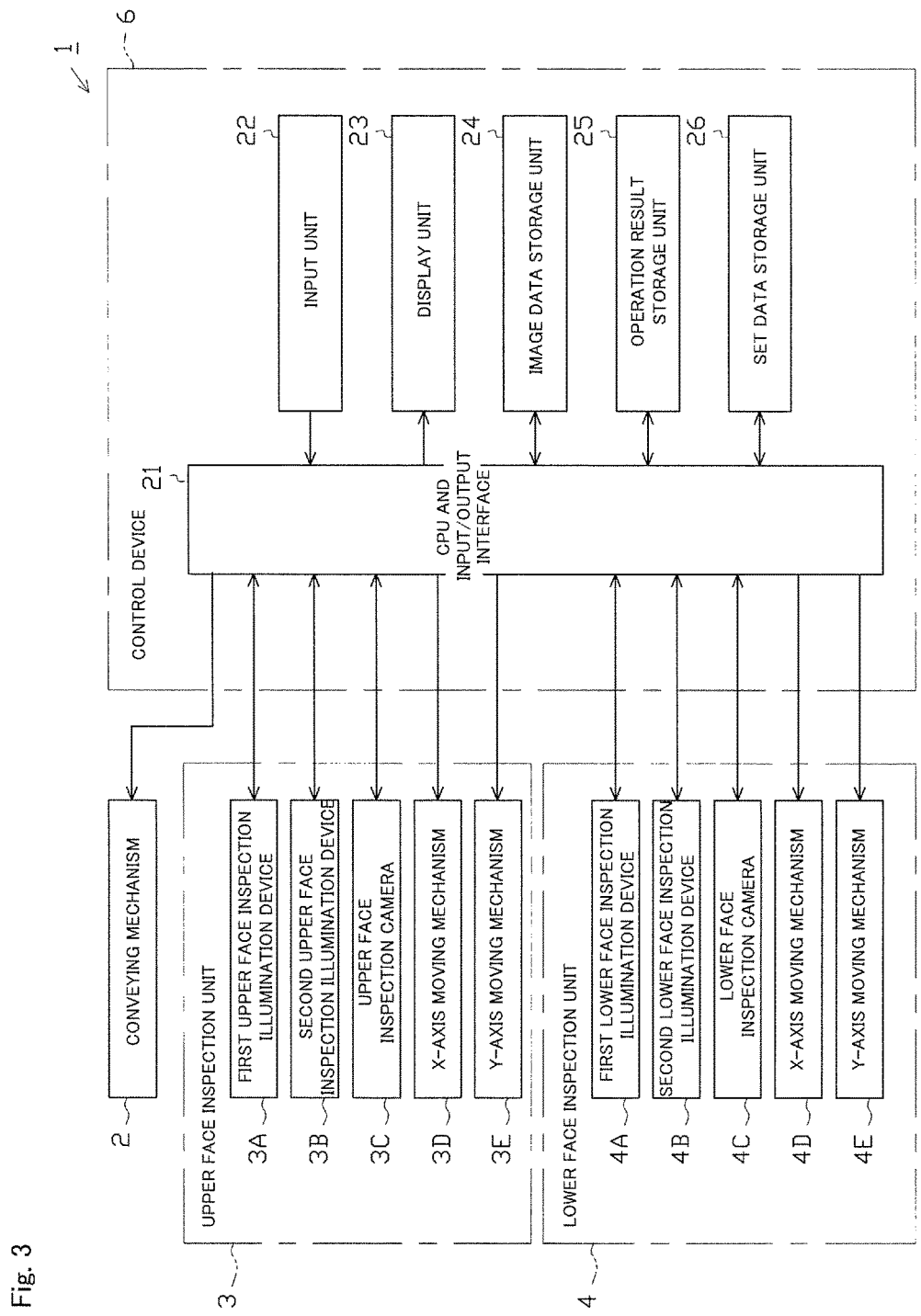
FIG. 3 is a block diagram illustrating the electrical configuration of the board inspection apparatus according to one or more embodiments of the invention.

The following describes the electrical configuration of the control device 6 with reference to FIG. 3. As shown in FIG. 3, the control device 6 includes a CPU and input/output interface 21 configured to control the entire board inspection apparatus 1 (hereinafter referred to as "CPU and the like 21"), an input unit 22 configured by, for example, a keyboard, a mouse and a touch panel and provided as "input means", a display unit 23 configured to have a display screen such as a CRT or liquid crystal screen and provided as "display means", an image data storage unit 24 or a memory configured to store image data and the like taken by the upper face inspection camera 3C and the lower face inspection camera 4C, an operation result storage unit 25 configured to store the results of various arithmetic operations, and a set data storage unit 26 configured to store in advance various information such as Gerber data (including information with regard to the recognition marks). These respective units 22 to 26 are electrically connected with the CPU and the like 21.

Pieces of information with regard to the plurality of inspection areas respectively set on both the upper face and the lower face of the printed circuit board P1 and sequences of inspection of these inspection areas are stored in the set data storage unit 26. The "sequence of inspection" herein specifies in which sequence the plurality of inspection areas set on the upper face (or the lower face) of the printed circuit board P1 are to be inspected. In other words, the "sequence of inspection" specifies in which sequence the imaging view KU of the upper face inspection camera 3C (or the imaging view KL of the lower inspection camera 4C) is to be moved with respect to the plurality of inspection areas.

The plurality of inspection areas on both the upper face and the lower face of the printed circuit board P1 and the sequences of inspection of these inspection areas may be set in advance automatically according to a predetermined program or may be set manually by an operator, based on the Gerber data and the like. For example, the sequence of inspection is set such that the upper face inspection unit 3 (or the lower face inspection unit 4) is moved by a shortest path from a predetermined starting point on the upper face (or the lower face) of the printed circuit board P1.

According to the embodiment, the sequence of inspection is set from a predetermined inspection area as the starting point. For example, in the example of the upper face side of the printed circuit board P1 shown in FIG. 6, the sequence of inspection is set from an inspection area at an upper right corner as the starting point. In the example of the lower face side of the printed circuit board P1, the sequence of inspection is set from an inspection area at an upper left corner as the starting point.

According to another configuration, for example, the sequence of inspection may be set, such that the upper face inspection unit 3 (or the lower face inspection unit 4) is moved by a shortest path from a recognition mark that is imaged later between the two recognition marks [A] and [B] (or [a] and [b]) on the upper face side (or the lower face side) of the printed circuit board P1 as the starting point.

Each area surrounded by a broken line frame in FIG. 6 represents an inspection area or an imaging view. The numerals "1" to "15" provided in the respective areas indicate the sequence of inspection. In FIG. 6, the moving directions (moving paths) of the upper face inspection unit 3 and the lower face inspection unit 4 are shown by arrows.

The following describes an inspection routine of the printed circuit board P1 by the board inspection apparatus 1. This inspection routine is performed by the control device 6 (CPU or the like 21).

According to this embodiment, an inspection process with regard to a predetermined inspection area on the upper face side of the printed circuit board P1 (one image acquisition process consisting of a plurality of imaging processes by the upper face inspection camera 3C) and an inspection process with regard to a predetermined inspection area on the lower face side of the printed circuit board P1 (one image acquisition process consisting of a plurality of imaging processes by the lower face inspection camera 4C) are performed alternately.

Figure 5A:
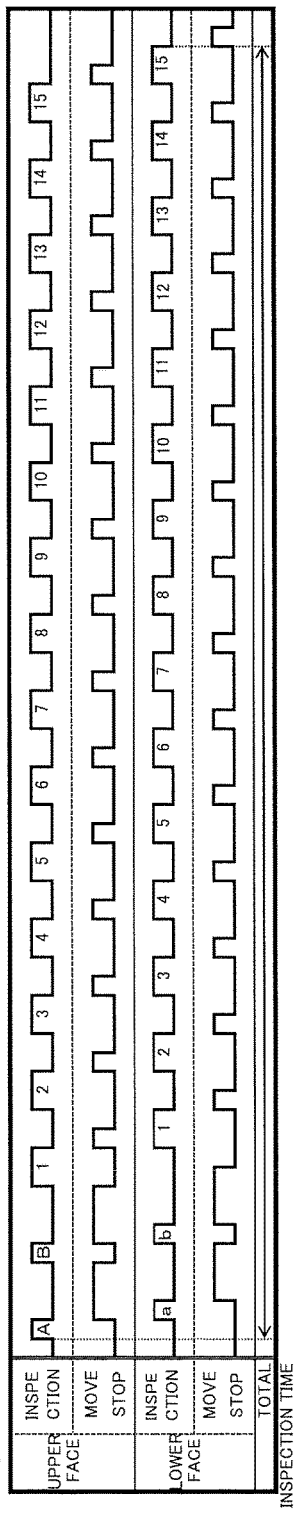
FIGS. 5A to 5C are timing charts illustrating processing operations of an upper face inspection unit and a lower face inspection unit according to one or more embodiments of the invention in inspection of both an upper face and a lower face of the printed circuit board.

These processes are described in detail below with reference to FIG. 5A and FIG. 6. FIG. 5A is a timing chart illustrating the processing operations of the upper face inspection unit 3 and the lower face inspection unit 4 to perform inspection processes (image acquisition processes) with regard to "$1^{st}$" to "$15^{th}$" inspection areas on the upper face side of the printed circuit board P1 and inspection processes (image acquisition processes) with regard to the "$1^{st}$" to "$15^{th}$", inspection areas on the lower face side of the printed circuit board P1.

The signs "A" and "B" in FIG. 5A respectively indicate that the first recognition mark [A] and the second recognition mark [B] on the upper face of the printed circuit board P1 shown in FIG. 6 are set as imaging objects. Similarly, the signs "a" and "b" in FIG. 5A respectively indicate that the first recognition mark [a] and the second recognition mark [b] on the lower face of the printed circuit board P1 shown in FIG. 6 are set as imaging objects. The numerals "1" to "15" in FIG. 5A respectively indicate that the "$1^{st}$" to the "$15^{th}$" inspection areas on the upper face and on the lower face of the printed circuit board P1 shown in FIG. 6 are set as imaging objects.

As described above, when the printed circuit board P1 carried into the board inspection apparatus 1 is located and fixed at a predetermined inspection position, the control device 6 first moves the upper face inspection unit 3 to adjust the imaging view KU of the upper face inspection camera 3C to the first recognition mark [A] on the upper face of the printed circuit board P1, while moving the lower face inspection unit 4 to adjust the imaging view KL of the lower face inspection camera 4C to the first recognition mark [a] on the lower face of the printed circuit board P1.

The control device 6 subsequently starts emission of light from the first upper face inspection illumination device 3A or the second upper face inspection illumination device 3B to take an image of the first recognition mark [A] on the upper face of the printed circuit board P1 in the state that emission of light from the lower face inspection unit 4 (from the first lower face inspection illumination device 4A and the second lower face inspection illumination device 4B) is stopped.

In the case of taking an image of the first recognition mark [A], the configuration irradiates the first recognition mark [A] with the light emitted from the light source 3Aa without the grid plate 3Ab and thereby not with a stripe pattern but with uniform light (the same applies when images of the other recognition marks are taken in the description below).

On termination of the imaging process of the first recognition mark [A] described above, the control device 6 starts a moving process to move the upper face inspection unit 3 to a position corresponding to the second recognition mark [B] on the upper face of the printed circuit board P1.

At the same time, the control device 6 starts emission of light from the first lower face inspection illumination device 4A or the second lower face inspection illumination device 4B to take an image of the first recognition mark [a] on the lower face of the printed circuit board P1 in the state that emission of light from the upper face inspection unit 3 (from the first upper face inspection illumination device 3A and the second upper face inspection illumination device 3B) is stopped.

On termination of the imaging process of the first recognition mark [a] described above, the control device 6 starts a moving process to move the lower face inspection unit 4 to a position corresponding to the second recognition mark [b] on the lower face of the printed circuit board P1.

When the moving process of the upper face inspection unit 3 is completed and the imaging view KU of the upper face inspection camera 3C is adjusted to the second recognition mark [B] on the upper face of the printed circuit board P1, the control device 6 starts emission of light from the first upper face inspection illumination device 3A or the second upper face inspection illumination device 3B to take an image of the second recognition mark [B] on the upper face of the printed circuit board P1 in the state that emission of light from the lower face inspection unit 4 (from the first lower face inspection illumination device 4A and the second lower face inspection illumination device 4B) is stopped.

On termination of the imaging process of the second recognition mark [B] described above, the control device 6 starts a moving process to move the upper face inspection unit 3 to a position corresponding to a "$1^{st}$" inspection area on the upper face of the printed circuit board P1 according to the sequence of inspection stored in the set data storage unit 26.

At the same time, the control device 6 starts emission of light from the first lower face inspection illumination device 4A or the second lower face inspection illumination device 4B to take an image of the second recognition mark [b] on the lower face of the printed circuit board P1 in the state that emission of light from the upper face inspection unit 3 (from the first upper face inspection illumination device 3A and the second upper face inspection illumination device 3B) is stopped.

On termination of the imaging process of the second recognition mark [b] described above, the control device 6 starts a moving process to move the lower face inspection unit 4 to a position corresponding to a "$1^{st}$" inspection area on the lower face of the printed circuit board P1 according to the sequence of inspection stored in the set data storage unit 26.

With regard to the upper face of the printed circuit board P1, on termination of the imaging processes of the first recognition mark [A] and the second recognition mark [B], the control device 6 computes deviations of the position coordinates of the first recognition mark [A] and the second recognition mark [B] related to the image data obtained by the imaging processes from the position coordinates of the first recognition mark [A] and the second recognition mark [B] related to the Gerber data and corrects the computed deviations during the moving process described above.

This corrects the deviation in the relative positional relationship between the upper face inspection unit 3 (upper face inspection camera 3C) and the upper face of the printed circuit board P1. This processing function implements the surface-side corrector according to the embodiment. According to another configuration, the correction of the deviations may not be performed during the moving process, but the moving process may be started to move the upper face inspection unit 3 to the position corresponding to the "$1^{st}$" inspection area on the upper face of the printed circuit board P1 after termination of the imaging process of the second recognition mark [B] and the subsequent correction of the deviations.

Similarly, with regard to the lower face of the printed circuit board P1, on termination of the imaging processes of the first recognition mark [a] and the second recognition mark [b], the control device 6 computes deviations of the position coordinates of the first recognition mark [a] and the second recognition mark [b] related to the image data obtained by the imaging processes from the position coordinates of the first recognition mark [a] and the second recognition mark [b] related to the Gerber data and corrects the computed deviations during the moving process described above.

This corrects the deviation in the relative positional relationship between the lower face inspection unit 4 (lower face inspection camera 4C) and the lower face of the printed circuit board P1. This processing function implements the rear face-side corrector according to the embodiment. According to another configuration, the correction of the deviations may not be performed during the moving process, but the moving process may be started to move the lower face inspection unit 4 to the position corresponding to the "$1^{st}$" inspection area on the lower face of the printed circuit board P1 after termination of the imaging process of the second recognition mark [b] and the subsequent correction of the deviations.

After that, when the moving process of the upper face inspection unit 3 is completed and the imaging view KU of the upper face inspection camera 3C is adjusted to the "$1^{st}$" inspection area on the upper face of the printed circuit board P1, the control device 6 starts emission of a stripe pattern from the first upper face inspection illumination device 3A or the second upper face inspection illumination device 3B and performs an image acquisition process with regard to the "$1^{st}$" inspection area on the upper face of the printed circuit board P1 in the state that emission of light from the lower face inspection unit 4 (from the first lower face inspection illumination device 4A and the second lower face inspection illumination device 4B) is stopped. The details of the image acquisition process will be described later (the same applies to the image acquisition process with regard to another inspection area).

In the meantime (i.e., during the execution time period of the image acquisition process with regard to the inspection area on the upper face of the printed circuit board P1), the moving process of the lower face inspection unit 4 described above (for example, the moving process to move the lower face inspection unit 4 to the position corresponding to the "$1^{st}$" inspection area on the lower face of the printed circuit board P1) is completed, and the imaging view KL of the lower face inspection camera 4C is adjusted to the "$1^{st}$" inspection area on the lower face of the printed circuit board P1.

After that, on termination of the image acquisition process with regard to the "$1^{st}$", inspection area on the upper face of the printed circuit board P1, the control device 6 starts a moving process to move the upper face inspection unit 3 to a position corresponding to a "$2^{nd}$" inspection area on the upper face of the printed circuit board P1 according to the sequence of inspection stored in the set data storage unit 26.

At the same time, the control device 6 starts emission of a stripe pattern from the first lower face inspection illumination device 4A or the second lower face inspection illumination device 4B and performs an image acquisition process with regard to the "$1^{st}$" inspection area on the lower face of the printed circuit board P1 in the state that emission of light from the upper face inspection unit 3 (from the first upper face inspection illumination device 3A and the second upper face inspection illumination device 3B) is stopped.

In the meantime (i.e., during the execution time period of the image acquisition process with regard to the "$1^{st}$" inspection area on the lower face of the printed circuit board P1), the moving process of the upper face inspection unit 3 described above (for example, the moving process to move the upper face inspection unit 3 to the position corresponding to the "$2^{nd}$" inspection area on the upper face of the printed circuit board P1) is completed, and the imaging view KU of the upper face inspection camera 3C is adjusted to the "$2^{nd}$" inspection area on the upper face of the printed circuit board P1.

After that, on termination of the image acquisition process with regard to the "$1^{st}$" inspection area on the lower face of the printed circuit board P1, the control device 6 starts a moving process to move the lower face inspection unit 4 to a position corresponding to a "$2^{nd}$" inspection area on the lower face of the printed circuit board P1 according to the sequence of inspection stored in the set data storage unit 26.

At the same time, the control device 6 starts emission of a stripe pattern from the first upper face inspection illumination device 3A or the second upper face inspection illumination device 3B and performs an image acquisition process with regard to the "$2^{nd}$" inspection area on the upper face of the printed circuit board P1 in the state that emission of light from the lower face inspection unit 4 (from the first lower face inspection illumination device 4A and the second lower face inspection illumination device 4B) is stopped.

In the meantime (i.e., during the execution time period of the image acquisition process with regard to the "2nd" inspection area on the upper face of the printed circuit board P1), the moving process of the lower face inspection unit 4 described above (for example, the moving process to move the lower face inspection unit 4 to the position corresponding to the "2nd" inspection area on the lower face of the printed circuit board P1) is completed, and the imaging view KL of the lower face inspection camera 4C is adjusted to the "2nd" inspection area on the lower face of the printed circuit board P1.

After that, on termination of the image acquisition process with regard to the "2nd" inspection area on the upper face of the printed circuit board P1, the control device 6 starts a moving process to move the upper face inspection unit 3 to a position corresponding to a "3rd" inspection area on the upper face of the printed circuit board P1 according to the sequence of inspection stored in the set data storage unit 26.

At the same time, the control device 6 starts emission of a stripe pattern from the first lower face inspection illumination device 4A or the second lower face inspection illumination device 4B and performs an image acquisition process with regard to the "2nd" inspection area on the lower face of the printed circuit board P1 in the state that emission of light from the upper face inspection unit 3 (from the first upper face inspection illumination device 3A and the second upper face inspection illumination device 3B) is stopped.

Subsequently, image acquisition processes with regard to "3rd" to "15th" inspection areas on the upper face of the printed circuit board P1 by the upper face inspection unit 3 and moving processes of the upper face inspection unit 3 between the image acquisition processes and image acquisition processes with regard to "3rd" to "15th" inspection areas on the lower face of the printed circuit board P1 by the lower face inspection unit 4 and moving processes of the lower face inspection unit 4 between the image acquisition processes are alternately performed in the similar manner. This completes inspection on both the upper face and the lower face of the printed circuit board P1.

The following describes the image acquisition process with regard to each inspection area on the upper face and on the lower face of the printed circuit board P1 performed by the board inspection apparatus 1. This image acquisition process is performed by the control device 6 (CPU and the like 21).

According to this embodiment, an image acquisition process is performed for inspection with regard to each of the inspection areas on the upper face side of the printed circuit board P1. The image acquisition process changes the phase of a stripe pattern that is emitted from the first upper face inspection illumination device 3A and performs four imaging processes with this stripe pattern of different phases. The image acquisition process subsequently changes the phase of a stripe pattern that is emitted from the second upper face inspection illumination device 3B and performs four imaging processes with this stripe pattern of different phases. This accordingly performs the image acquisition process to obtain a total of eight different image data.

Similarly, an image acquisition process is performed for inspection with regard to each of the inspection areas on the lower face side of the printed circuit board P1. The image acquisition process changes the phase of a stripe pattern that is emitted from the first lower face inspection illumination device 4A and performs four imaging processes with this stripe pattern of different phases. The image acquisition process subsequently changes the phase of a stripe pattern that is emitted from the second lower face inspection illumination device 4B and performs four imaging processes with this stripe pattern of different phases. This accordingly performs the image acquisition process to obtain a total of eight different image data.

Figure 4:
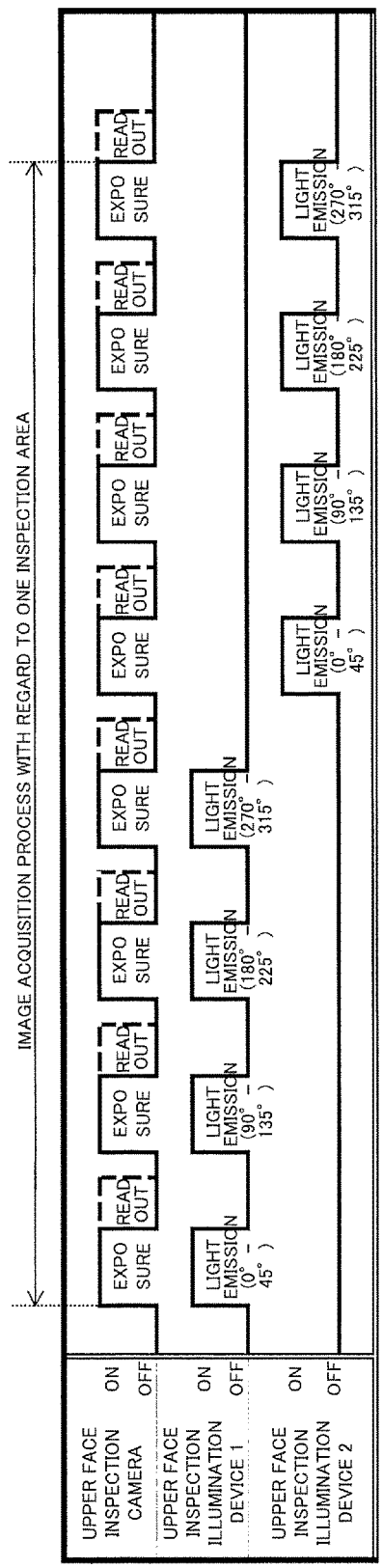
FIG. 4 is a timing chart illustrating an image acquisition process with regard to one inspection area according to one or more embodiments of the invention.

The following describes the inspection routine (image acquisition process) performed with regard to each of the inspection areas in inspection on the upper face side of the printed circuit board P1 as an example with reference to FIG. 4.

When the imaging view KU of the upper face inspection camera 3C is adjusted to a predetermined inspection area on the upper face of the printed circuit board. P1, the control device 6 drives and controls the first upper face inspection illumination device 3A to set the position of the grid plate 3Ab to a default position (position at which the phase of the stripe pattern projected in a predetermined location is equal to "0 degree"). At the same time, the control device 6 drives and controls the second upper face inspection illumination device 3B to set the position of the grid plate 3Bb to a default position (position at which the phase of the stripe pattern projected in the predetermined location is equal to "0 degree").

After completion of such setting, the control device 6 drives and controls the first upper face inspection illumination device 3A and the upper face inspection camera 3C to start a first imaging process (exposure process) with a stripe pattern that is emitted from the first upper face inspection illumination device 3A.

For example, the control device 6 triggers light emission from the light source 3Aa of the first upper face inspection illumination device 3A so as to start emission of a stripe pattern and also starts the moving process of the grid plate 3Ab. This causes the stripe pattern that is projected in the inspection area to be continuously shifted at a constant speed along the Y-axis direction.

The control device 6 then starts an imaging process using the upper face inspection camera 3C, simultaneously with starting the emission of the stripe pattern (and starting the move of the grid plate 3Ab).

After the start of this first imaging process, the exposure is continued, while the phase of the stripe pattern projected in the predetermined location is changed from 0 degree to 45 degrees.

On termination of the first imaging process, the control device 6 stops the emission of light from the light source 3Aa and reads out image data taken by the upper face inspection camera 3C. The image data is then transferred from the upper face inspection camera 3C to the control device 6. The control device 6 stores the read-out image data into the image data storage unit 24.

The moving process of the grid plate 3Ab is, on the other hand, not terminated even after termination of the first imaging process, but is continued without any interruption until termination of a fourth imaging process with the stripe pattern that is emitted from the upper face inspection illumination device 3A.

Image data having a light intensity distribution in a sinusoidal wave form is obtained by continuously shifting the stripe pattern that is projected on the printed circuit board P1 and has the light intensity distribution in a square wave form or in a trapezoidal wave form and continuing imaging (exposure) of the stripe pattern (as described in Japanese Patent Application No. 2015-231661).

After elapse of a predetermined time period since termination of the first imaging process, at the timing when the phase of the stripe pattern that is to be projected in the predetermined location becomes equal to 90 degrees, the control device 6 again triggers light emission from the light source 3Aa of the first upper face inspection illumination device 3A so as to start emission of the stripe pattern and also starts an imaging process using the upper face inspection camera 3C. This starts a second imaging process with the stripe pattern that is emitted from the first upper face inspection illumination device 3A.

After the start of this second imaging process, the exposure is continued, while the phase of the stripe pattern projected in the predetermined location is changed from 90 degrees to 135 degrees.

On termination of the second imaging process, the control device 6 stops the emission of light from the light source 3Aa, reads out image data taken by the upper face inspection camera 3C, and stores the read-out image data into the image data storage unit 24.

After elapse of a predetermined time period since termination of the second imaging process, at the timing when the phase of the stripe pattern that is to be projected in the predetermined location becomes equal to 180 degrees, the control device 6 again triggers light emission from the light source 3Aa of the first upper face inspection illumination device 3A so as to start emission of the stripe pattern and also starts an imaging process using the upper face inspection camera 3C. This starts a third imaging process with the stripe pattern that is emitted from the first upper face inspection illumination device 3A.

After the start of this third imaging process, the exposure is continued, while the phase of the stripe pattern projected in the predetermined location is changed from 180 degrees to 225 degrees.

On termination of the third imaging process, the control device 6 stops the emission of light from the light source 3Aa, reads out image data taken by the upper face inspection camera 3C, and stores the read-out image data into the image data storage unit 24.

After elapse of a predetermined time period since termination of the third imaging process, at the timing when the phase of the stripe pattern that is to be projected in the predetermined location becomes equal to 270 degrees, the control device 6 again triggers light emission from the light source 3Aa of the first upper face inspection illumination device 3A so as to start emission of the stripe pattern and also starts an imaging process using the upper face inspection camera 3C. This starts a fourth imaging process with the stripe pattern that is emitted from the first upper face inspection illumination device 3A.

After the start of this fourth imaging process, the exposure is continued, while the phase of the stripe pattern projected in the predetermined location is changed from 270 degrees to 315 degrees.

On termination of the fourth imaging process, the control device 6 stops the emission of light from the light source 3Aa, reads out image data taken by the upper face inspection camera 3C, and stores the read-out image data into the image data storage unit 24. Additionally, the control device 6 terminates the moving process of the grid plate 3Ab.

After elapse of a predetermined time period since termination of the fourth imaging process (for example, after termination of a data transfer period), the control device 6 drives and controls the second upper face inspection illumination device 3B and the upper face inspection camera 3C to start a fifth imaging process with regard to the predetermined inspection area (i.e., a first imaging process with a stripe pattern that is emitted from the second upper face inspection illumination device 3B).

For example, the control device 6 triggers light emission from the light source 3Ba of the second upper face inspection illumination device 3B so as to start emission of a stripe pattern and also starts the moving process of the grid plate 3Bb. This causes the stripe pattern that is projected in the inspection area to be continuously shifted at a constant speed along the Y-axis direction.

The control device 6 then starts an imaging process using the upper face inspection camera 3C, simultaneously with starting the emission of the stripe pattern (and starting the move of the grid plate 3Bb).

After the start of this fifth imaging process, the exposure is continued, while the phase of the stripe pattern projected in the predetermined location is changed from 0 degree to 45 degrees.

On termination of the fifth imaging process, the control device 6 stops the emission of light from the light source 3Ba and reads out image data taken by the upper face inspection camera 3C. The image data is then transferred from the upper face inspection camera 3C to the control device 6. The control device 6 stores the read-out image data into the image data storage unit 24.

The moving process of the grid plate 3Bb is, on the other hand, not terminated even after termination of the fifth imaging process (i.e., the first imaging process with the stripe pattern that is emitted from the second upper face inspection illumination device 3B), but is continued without any interruption until termination of an eighth imaging process with regard to the predetermined inspection area (i.e., a fourth imaging process with the stripe pattern that is emitted from the second upper face inspection illumination device 3B).

After elapse of a predetermined time period since termination of the fifth imaging process, at the timing when the phase of the stripe pattern that is to be projected in the predetermined location becomes equal to 90 degrees, the control device 6 again triggers light emission from the light source 3Ba of the second upper face inspection illumination device 3B so as to start emission of the stripe pattern and also starts an imaging process using the upper face inspection camera 3C. This starts a sixth imaging process with regard to the predetermined inspection area (i.e., a second imaging process with the stripe pattern that is emitted from the second upper face inspection illumination device 3B).

After the start of this sixth imaging process, the exposure is continued, while the phase of the stripe pattern projected in the predetermined location is changed from 90 degrees to 135 degrees.

On termination of the sixth imaging process, the control device 6 stops the emission of light from the light source 3Ba, reads out image data taken by the upper face inspection camera 3C, and stores the read-out image data into the image data storage unit 24.

After elapse of a predetermined time period since termination of the sixth imaging process, at the timing when the phase of the stripe pattern that is to be projected in the predetermined location becomes equal to 180 degrees, the control device 6 again triggers light emission from the light source 3Ba of the second upper face inspection illumination device 3B so as to start emission of the stripe pattern and also starts an imaging process using the upper face inspection camera 3C. This starts a seventh imaging process with regard to the predetermined inspection area (i.e., a third imaging process with the stripe pattern that is emitted from the second upper face inspection illumination device 3B).

After the start of this seventh imaging process, the exposure is continued, while the phase of the stripe pattern projected in the predetermined location is changed from 180 degrees to 225 degrees.

On termination of the seventh imaging process, the control device 6 stops the emission of light from the light source 3Ba, reads out image data taken by the upper face inspection camera 3C, and stores the read-out image data into the image data storage unit 24.

After elapse of a predetermined time period since termination of the seventh imaging process, at the timing when the phase of the stripe pattern that is to be projected in the predetermined location becomes equal to 270 degrees, the control device 6 again triggers light emission from the light source 3Ba of the second upper face inspection illumination device 3B so as to start emission of the stripe pattern and also starts an imaging process using the upper face inspection camera 3C. This starts an eighth imaging process with regard to the predetermined inspection area (i.e., a fourth imaging process with the stripe pattern that is emitted from the second upper face inspection illumination device 3B).

After the start of this eighth imaging process, the exposure is continued, while the phase of the stripe pattern projected in the predetermined location is changed from 270 degrees to 315 degrees.

On termination of the eighth imaging process, the control device 6 stops the emission of light from the light source 3Ba, reads out image data taken by the upper face inspection camera 3C, and stores the read-out image data into the image data storage unit 24. Additionally, the control device 6 terminates the moving process of the grid plate 3Bb and then terminates the image acquisition process with regard to the predetermined inspection area.

Performing the image acquisition process (eight imaging processes) described above results in obtaining a total of eight different image data including four different image data taken with the stripe pattern that is emitted from the first upper face inspection illumination device 3A and four different image data taken with the stripe pattern that is emitted from the second upper face inspection illumination device 3B.

As described above, according to this embodiment, the four different image data taken with each of the stripe patterns are equivalent to four different image data taken by successively shifting the phase of a stripe pattern having a light intensity distribution in a sinusoidal wave form by 90 degrees each.

The control device 6 subsequently performs three-dimensional measurement (measurement of height) by a known phase shift method, based on the four different image data (luminance values of respective pixels) taken with each of the stripe patterns, and stores the result of this measurement into the operation result storage unit 25. According to this embodiment, the three-dimensional measurement is performed with emission of the stripe pattern from two different directions. This prevents the occurrence of any shaded area without emission of the stripe pattern.

The control device 6 subsequently performs a quality determination process of the solder paste P4, based on the result of the three-dimensional measurement (height data at each coordinate). For example, the control device 6 detects a printing range of the solder paste P4 that is higher than a reference plane, based on the result of the measurement with regard to the predetermined inspection area obtained as described above, and integrates the heights in respective locations in this printing range, so as to calculate the printed amount of the solder paste P4.

The control device 6 then compares the data obtained as described above with regard to the solder paste P4, for example, the location, the area and the height or the amount of the solder paste P4, with reference data (for example, Gerber data) stored in advance in the set data storage unit 26 and determines whether the printing state of the solder paste P4 is good or not with regard to the predetermined inspection area, based on whether the result of the comparison is within an allowable range.

After termination of the eighth imaging process described above, the control device 6 moves the upper face inspection unit 3 to a next inspection area, while performing the quality determination process described above. Repeating the series of processing described above with regard to all the inspection areas on the upper face of the printed circuit board P1 results in completing inspection of the entire upper face of the printed circuit board P1. The flow of inspection on the lower face side of the printed circuit board P1 is similar to the flow of inspection on the upper face side, so that its detailed description is omitted.

As described above in detail, after performing the image acquisition process with regard to a predetermined inspection area on the upper face side (or the lower face side) of the printed circuit board P1, the configuration of this embodiment moves the upper face inspection unit 3 (or the lower face inspection unit 4) to a position corresponding to a next inspection area and performs the image acquisition process with regard to a predetermined inspection area on the lower face side (or the upper face side) of the printed circuit board P1.

In other words, this configuration alternately repeats the image acquisition process with regard to a predetermined inspection area on the upper face side of the printed circuit board P1 and the image acquisition process with regard to a predetermined inspection area on the lower face side of the printed circuit board P1. This enables the image acquisition processes with regard to a plurality of inspection areas on the entire area of the upper face side of the printed circuit board P1 and the image acquisition processes with regard to a plurality of inspection areas on the entire area of the lower face side of the printed circuit board P1 to be performed at the same time.

Figure 9:
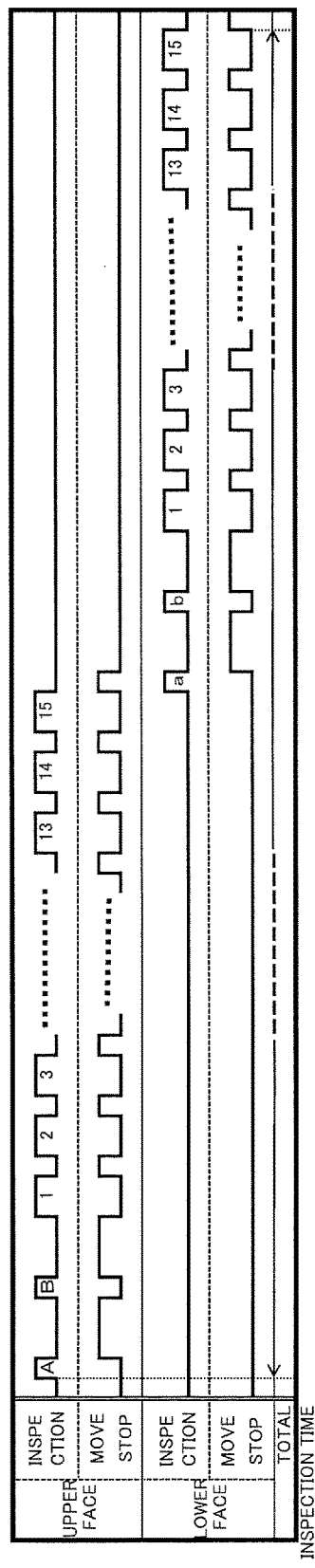
FIG. 9 is a timing chart showing processing operations of a prior art upper face inspection unit and a prior art lower face inspection unit in inspection of both the upper face and the lower face of the printed circuit board.

Compared with a configuration that performs the image acquisition processes with regard to a plurality of inspection areas on the entire area of the lower face side of the printed circuit board P1 after completion of the image acquisition processes with regard to a plurality of inspection areas on the entire area of the upper face side of the printed circuit board P1 like a prior art example shown in FIG. 9, this configuration increases the inspection speed with regard to double-sided inspection of the printed circuit board P.

The configuration of this embodiment stops emission of light on the lower face side (or on the upper face side) during an image acquisition period with regard to a predetermined inspection area on the upper face side (or the lower face side) of the printed circuit board P1. This configuration enables image data of the high accuracy to be obtained without causing leakage of light to the upper face side (or to the lower face side). This results in improving the inspection accuracy with regard to double-sided inspection of the printed circuit board P1.

As a result, this improves the inspection accuracy and increases the inspection speed with regard to double-sided inspection of the printed circuit board P1.

Second Embodiment

Figure 5B:
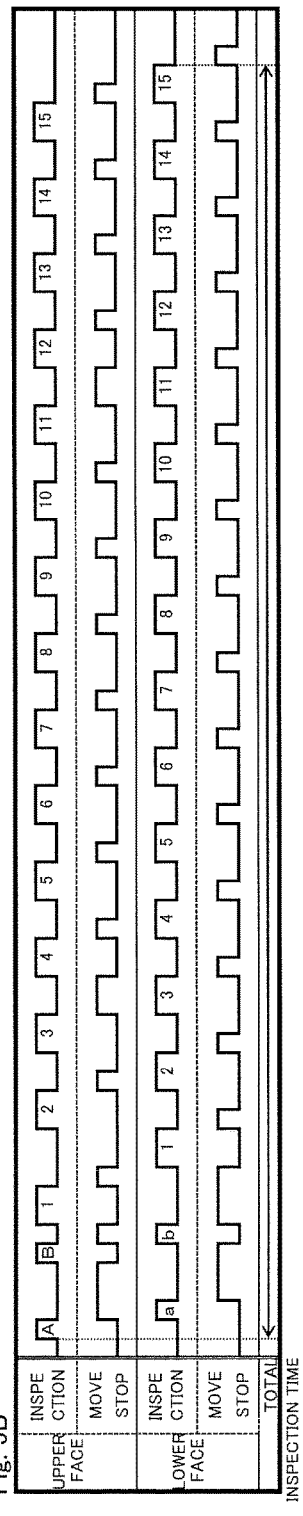
Figure 7:
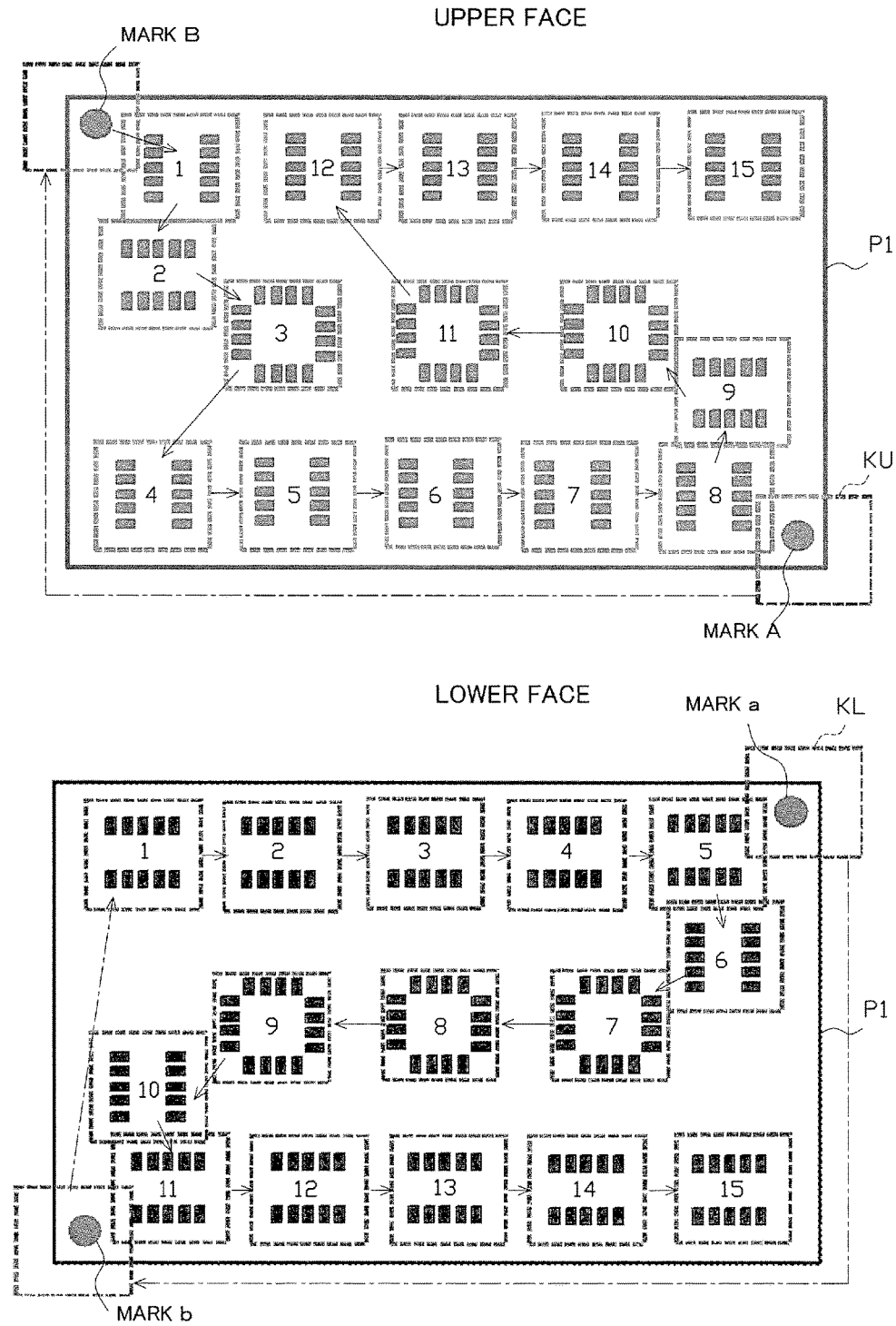
FIG. 7 is a diagram illustrating sequences of inspection on the upper face side and on the lower face side of the printed circuit board according to one or more embodiments of the invention.

The following describes a second embodiment with reference to FIG. 5B and FIG. 7. FIG. 5B is a timing chart illustrating the processing operations of the upper face inspection unit 3 and the lower face inspection unit 4 according to this embodiment. FIG. 7 is a diagram illustrating sequences of inspection on the upper face side and on the lower face side of the printed circuit board P1 (moving paths of the upper face inspection unit 3 and the lower face inspection unit 4) according to this embodiment. The like components to those of the first embodiment are expressed by the like signs, and their detailed description is omitted.

The second embodiment employs a sequence of inspection on the upper face side of the printed circuit board P1 (moving path of the upper face inspection unit 3) that is different from that of the first embodiment. The second embodiment, on the other hand, employs a sequence of inspection on the lower face side of the printed circuit board P1 (moving path of the lower face inspection unit 4) that is identical with that of the first embodiment.

The control device 6 first moves the upper face inspection unit 3 to adjust the imaging view KU of the upper face inspection camera 3C to the first recognition mark [A] on the upper face of the printed circuit board P1, while moving the lower face inspection unit 4 to adjust the imaging view KL of the lower face inspection camera 4C to the first recognition mark [a] on the lower face of the printed circuit board P1.

The control device 6 subsequently takes an image of the first recognition mark [A] on the upper face of the printed circuit board P1. On termination of this imaging process, the control device 6 starts a moving process to move the upper face inspection unit 3 to a position corresponding to the second recognition mark [B] on the upper face of the printed circuit board P1.

At the same time, the control device 6 takes an image of the first recognition mark [a] on the lower face of the printed circuit board P1. On termination of this imaging process, the control device 6 starts a moving process to move the lower face inspection unit 4 to a position corresponding to the second recognition mark [b] on the lower face of the printed circuit board P1.

After that, when the moving process of the upper face inspection unit 3 is completed and the imaging view KU of the upper face inspection camera 3C is adjusted to the second recognition mark [B] on the upper face of the printed circuit board P1, the control device 6 takes an image of the second recognition mark [B] on the upper face of the printed circuit board P1.

On termination of this imaging process, the control device 6 starts a moving process to move the upper face inspection unit 3 to a position corresponding to a "$1^{st}$" inspection area on the upper face of the printed circuit board P1 according to the sequence of inspection stored in the set data storage unit 26.

According to this embodiment, an inspection area in a shortest distance from the second recognition mark [B] that is imaged later between the first recognition mark [A] and the second recognition mark [B] is set as the "$1^{st}$" inspection area for which the image acquisition process is to be performed first. In the example of the upper face side of the printed circuit board P1 shown in FIG. 7, an inspection area at an upper left corner is set as the "$1^{st}$" inspection area. The sequence of inspection is set such that the moving path of the upper face inspection unit 3 from this "$1^{st}$" inspection area as the starting point is a shortest path.

Simultaneously with starting the moving process of the upper face inspection unit 3 described above, the control device 6 takes an image of the second recognition mark [b] on the lower face of the printed circuit board P1. On termination of this imaging process, the control device 6 starts a moving process to move the lower face inspection unit 4 to a position corresponding to a "$1^{st}$" inspection area on the lower face of the printed circuit board P1 according to the sequence of inspection stored in the set data storage unit 26.

According to this embodiment, with respect to the lower face side of the printed circuit board P1, an inspection area in a shortest distance from the second recognition mark [b] that is imaged later between the first recognition mark [a] and the second recognition mark [b] is not set as the "$1^{st}$" inspection area for which the image acquisition process is to be performed first. The sequence of inspection on the lower face side of the printed circuit board P1 (moving path of the lower face inspection unit 4) is identical with the sequence of inspection in the first embodiment. Accordingly, in the example of the lower face side of the printed circuit board P1 shown in FIG. 7, an inspection area at an upper left corner is set as the "$1^{st}$" inspection area. The sequence of inspection is set such that the moving path of the lower face inspection unit 4 from this "$1^{st}$" inspection area as the starting point is a shortest path.

Simultaneously with starting the moving process of the lower face inspection unit 4 described above, when the moving process of the upper face inspection unit 3 is completed and the imaging view KU of the upper face inspection camera 3C is adjusted to the "$1^{st}$" inspection area on the upper face of the printed circuit board P1, the control device 6 performs an image acquisition process with regard to the "$1^{st}$" inspection area on the upper face of the printed circuit board P1.

On termination of this image acquisition process, the control device 6 starts a moving process to move the upper face inspection unit 3 to a position corresponding to a "$2^{nd}$" inspection area on the upper face of the printed circuit board P1 according to the sequence of inspection stored in the set data storage unit 26.

After that, when the moving process of the lower face inspection unit 4 is completed and the imaging view KL of the lower face inspection camera 4C is adjusted to the "$1^{st}$" inspection area on the lower face of the printed circuit board P1, the control device 6 performs an image acquisition process with regard to the "$1^{st}$" inspection area on the lower face of the printed circuit board P1.

Subsequently, image acquisition processes with regard to "$2^{nd}$" to "$15^{th}$" inspection areas on the upper face of the printed circuit board P1 by the upper face inspection unit 3 and moving processes of the upper face inspection unit 3 between the image acquisition processes and image acquisition processes with regard to "$2^{nd}$" to "$15^{th}$" inspection areas on the lower face of the printed circuit board P1 by the lower face inspection unit 4 and moving processes of the lower face inspection unit 4 between the image acquisition processes are alternately performed like the first embodiment. This completes inspection on both the upper face and the lower face of the printed circuit board P1.

As described above in detail, with respect to the upper face side of the printed circuit board P1, the configuration of this embodiment starts inspection from the inspection area located nearest to the second recognition mark [B] that is imaged later between the first recognition mark [A] and the second recognition mark [B]. This shortens the time period elapsed until a start of inspection with respect to the first inspection area and thereby increases the speed of inspection.

As described above, according to this embodiment, with respect to the lower face side of the printed circuit board P1, the inspection area in the shortest distance from the second recognition mark [b] that is imaged later between the first recognition mark [a] and the second recognition mark [b] is not set as the "$1^{st}$" inspection area for which the image acquisition process is to be performed first. According to another embodiment, with respect to the sequence of inspection on the lower face side of the printed circuit board P1 (moving path of the lower face inspection unit 4) in addition to the sequence of inspection on the upper face side of the printed circuit board P1, inspection may be started from an inspection area located nearest to the second recognition mark [b] that is imaged later between the first recognition mark [a] and the second recognition mark [b]. For example, in the example of the lower face side of the printed circuit board P1 shown in FIG. 7, an inspection area at a lower left corner may be set as the "$1^{st}$" inspection area.

According to another modification, on the contrary, the sequence of inspection on the upper face side of the printed circuit board P1 may be set to be identical with the sequence of inspection of the first embodiment. With respect to only the sequence of inspection on the lower face side of the printed circuit board P1 (moving path of the lower face inspection unit 4), inspection may be started from an inspection area located nearest to the second recognition mark [b] that is imaged later between the first recognition mark [a] and the second recognition mark [b].

Third Embodiment

Figure 5C:
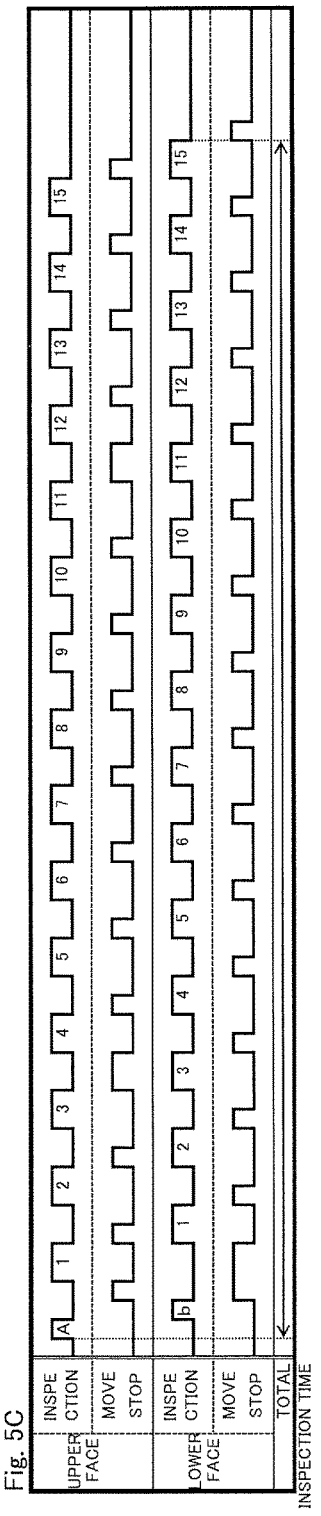
Figure 8:
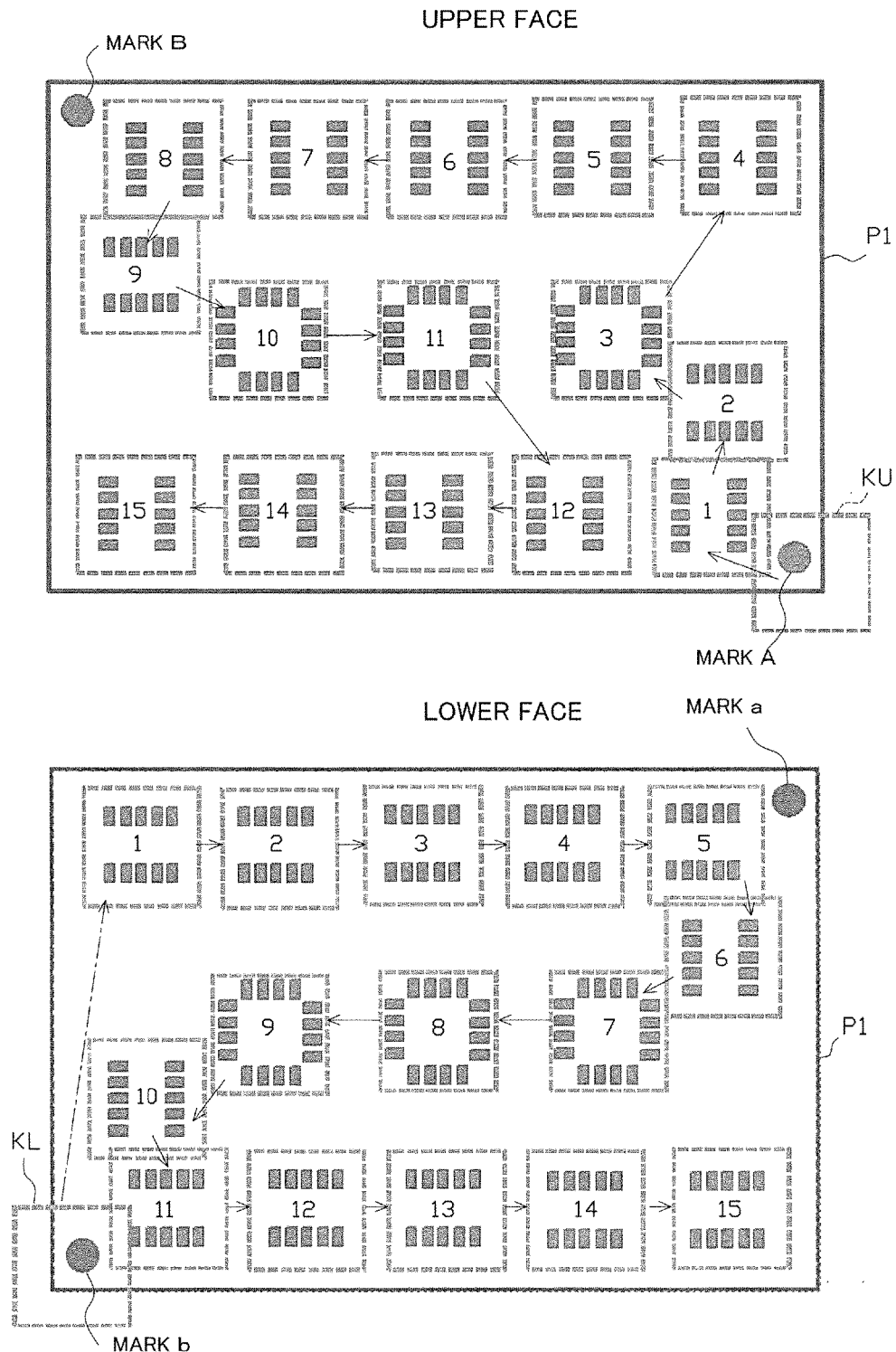
FIG. 8 is a diagram illustrating sequences of inspection on the upper face side and on the lower face side of the printed circuit board according to one or more embodiments of the invention.

The following describes a third embodiment with reference to FIG. 5C and FIG. 8. FIG. 5C is a timing chart illustrating the processing operations of the upper face inspection unit 3 and the lower face inspection unit 4 according to this embodiment. FIG. 8 is a diagram illustrating sequences of inspection on the upper face side and on the lower face side of the printed circuit board P1 (moving paths of the upper face inspection unit 3 and the lower face inspection unit 4) according to this embodiment. The like components to those of the first embodiment are expressed by the like signs, and their detailed description is omitted.

Correction of the positions with regard to both the upper face and the lower face of the printed circuit board P1 and the relevant processes (for example, procedure of imaging the recognition marks) of the third embodiment differ from those of the first embodiment.

The control device 6 first moves the upper face inspection unit 3 to adjust the imaging view KU of the upper face inspection camera 3C to the first recognition mark [A] on the upper face of the printed circuit board P1, while moving the lower face inspection unit 4 to adjust the imaging view KL of the lower face inspection camera 4C to the second recognition mark [b] on the lower face of the printed circuit board P1.

The control device 6 subsequently takes an image of the first recognition mark [A] on the upper face of the printed circuit board P1. On termination of this imaging process, the control device 6 takes an image of the second recognition mark [b] on the lower face of the printed circuit board P1.

On termination of this imaging process, the control device 6 starts a moving process to move the upper face inspection unit 3 to a position corresponding to a "$1^{st}$" inspection area on the upper face of the printed circuit board P1, while starting a moving process to move the lower face inspection unit 4 to a position corresponding to a "$1^{st}$" inspection area on the lower face of the printed circuit board P1, according to the sequence of inspection stored in the set data storage unit 26.

According to this embodiment, with regard to the upper face side of the printed circuit board P1, an inspection area in a shortest distance from the first recognition mark [A] is set as the "$1^{st}$" inspection area for which the image acquisition process is to be performed first. In the example of the upper face side of the printed circuit board P1 shown in FIG. 8, an inspection area at a lower right corner is set as the "$1^{st}$" inspection area. The sequence of inspection is set such that the moving path of the upper face inspection unit 3 from this "$1^{th}$" inspection area as the starting point is a shortest path.

With respect to the lower face side of the printed circuit board P1, on the other hand, an inspection area in a shortest distance from the second recognition mark [b] is not set as the "$1^{st}$" inspection area for which the image acquisition process is to be performed first. In the example of the lower face side of the printed circuit board P1 shown in FIG. 8, an inspection area at an upper left corner is set as the "$1^{st}$" inspection area. The sequence of inspection is set such that the moving path of the lower face inspection unit 4 from this "$1^{st}$" inspection area as the starting point is a shortest path.

On termination of the imaging process of the first recognition mark [A] on the upper face of the printed circuit board P1 and the imaging process of the second recognition mark [b] on the lower face of the printed circuit board P1, the control device 6 corrects the deviation in the relative positional relationship between the upper face inspection unit 3 and the upper face of the printed circuit board P1 and also corrects the deviation in the relative positional relationship between the lower face inspection unit 4 and the lower face of the printed circuit board P1 during the moving processes described above by taking into account the Gerber data, based on the position coordinates of the first recognition mark [A] on the upper face of the printed circuit board P1 and the position coordinates of the second recognition mark [b] on the lower face of the printed circuit board P1 related to the image data obtained by the above imaging processes and offset amounts of the upper face inspection unit 3 and the lower face inspection unit 4 (i.e., offset amounts of the upper face inspection camera 3C and the lower face inspection camera 4C) stored in advance in the set data storage unit 26. This processing function implements the corrector according to this embodiment. The offset amounts of the upper face inspection unit 3 and the lower face inspection unit 4 are determined in advance by calibration or the like prior to a start of inspection.

After that, when the moving process of the upper face inspection unit 3 is completed and the imaging view KU of the upper face inspection camera 3C is adjusted to the "$1^{st}$" inspection area on the upper face of the printed circuit board P1, the control device 6 performs an image acquisition process with regard to the "$1^{st}$" inspection area on the upper face of the printed circuit board P1.

On termination of this image acquisition process, the control device 6 starts a moving process to move the upper face inspection unit 3 to a position corresponding to a "$1^{st}$" inspection area on the upper face of the printed circuit board P1 according to the sequence of inspection stored in the set data storage unit 26.

At the same time, when the moving process of the lower face inspection unit 4 is completed and the imaging view KL of the lower face inspection camera 4C is adjusted to the "$1^{st}$" inspection area on the lower face of the printed circuit board P1, the control device 6 performs an image acquisition process with regard to the "$1^{st}$" inspection area on the lower face of the printed circuit board P1.

Subsequently, image acquisition processes with regard to "$2^{nd}$" to "$15^{th}$" inspection areas on the upper face of the printed circuit board P1 by the upper face inspection unit 3 and moving processes of the upper face inspection unit 3 between the image acquisition processes and image acquisition processes with regard to "$2^{nd}$" to "$15^{th}$" inspection areas on the lower face of the printed circuit board P1 by the lower face inspection unit 4 and moving processes of the lower face inspection unit 4 between the image acquisition processes are alternately performed like the first embodiment. This completes inspection on both the upper face and the lower face of the printed circuit board P1.

As described above in detail, the configuration of the embodiment uses the position information of the recognition mark with regard to one face out of the upper face and the lower face of the printed circuit board P1 as the position information with regard to the other face and thereby allows for the correction of positions by taking an image of only one recognition mark (i.e., without taking images of a plurality of recognition marks) on each of the upper face and the lower face of the printed circuit board P1. This further improves the inspection accuracy with respect to double-sided inspection of the printed circuit board P1.

This configuration starts inspection without taking images of a plurality of recognition marks on each of the upper face and the lower face of the printed circuit board P1 and thereby increases the speed of inspection.

The configuration of this embodiment performs the correction described above based on the offset amounts of the upper face inspection unit 3 and the lower face inspection unit 4, on the assumption that there is no positional misalignment (for example, stacking deviation or misalignment of patterns) between the upper face and the lower face of the printed circuit board P1. When there is a positional misalignment between the upper face and the lower face of the printed circuit board P1, the correction described above may be performed, for example, by obtaining in advance information on the positional misalignment between the surface and the rear face of the printed circuit board P1 (i.e., relative positional relationship between the surface and the rear face of the printed circuit board P1) detected in a previous process (for example, pattern inspection process) and management information (for example, serial number) of the printed circuit board P1.

For example, a through hole formed to pass through the printed circuit board P1 between the surface and the rear face may be used as the specified object for positioning, in place of the recognition mark described above. This allows for the above correction without taking into account the positional misalignment between the upper face and the lower face of the printed circuit board P1.

The present disclosure is not limited to the description of the above embodiments but may be implemented, for example, by aspects described below. The following description is, however, also only illustrative and the present disclosure may naturally be implemented by any other applications and modifications.

(a) According to each of the above embodiments, the board inspection apparatus is implemented as the solder printing inspection apparatus configured to perform an inspection for the printing state of the solder paste P4 printed on the printed circuit board P1. The board inspection apparatus is, however, not limited to this configuration but may be configured to perform an inspection for another object, for example, a solder bump printed on a board or an electronic component mounted on a board. The board inspection apparatus is also not limitedly used for inspection prior to reflow but may be used for inspection after reflow.

(b) Each of the above embodiments is configured to obtain four different image data with a stripe pattern of different phases shifted by 90 degrees each for three-dimensional measurement by the phase shift method. The number of phase shifts and the amount of each phase shift are, however, not limited to those of this embodiment. Any other allowable number of phase shifts and any other allowable amount of each phase shift may be employed for three-dimensional measurement by the phase shift method.

For example, one modified configuration may obtain three different image data having different phases shifted by 120 degrees each (or by 90 degrees each) for three-dimensional measurement. Another modified configuration may obtain two different image data having different phases shifted by 180 degrees each (or by 90 degrees each) for three-dimensional measurement.

(c) Each of the above embodiments is configured to continuously shift the stripe pattern that is projected on the printed circuit board P1 and has a light intensity distribution in a square wave form or in a trapezoidal wave form and continue imaging (exposure) of the stripe pattern, so as to obtain image data having a light intensity distribution in a sinusoidal wave form.

The imaging period in which imaging is to be continued is not limited to the time period of the above embodiment (corresponding to the move by the phase of 45 degrees), but a different configuration may be employed for this imaging period.

The configuration that continues imaging (exposure) is not essential. Like the prior art, one modified configuration may successively change the position of a grid and emit a stripe pattern in the state that the grid is at stop, so as to obtain a plurality of image data having different phases.

According to each of the above embodiments, the grid plate is employed as the means for converting light emitted from a light source into a stripe pattern. This is, however, not restrictive, and any other suitable means, for example, a liquid crystal panel configured to control the transmittance or the reflectance with respect to each reed-shaped line, may be employed. Using such a liquid crystal panel or the like allows for emission of a stripe pattern having a light intensity distribution in an ideal sinusoidal wave form without continuously moving a grid plate.

(d) Each of the above embodiments is configured to perform three-dimensional measurement by the phase shift method. The phase shift method is, however, not essential but another three-dimensional measurement method, for example, a space code method, may be employed. It is also beneficial to employ a measurement method of the high measurement accuracy, for example, the phase shift method, for measurement of a small measurement object such as the solder paste P4.

(e) The configuration involved in the irradiator, for example, the type of light emitted from each illumination device, is not limited to the configuration of the above embodiment, but another configuration may be employed.

For example, each of the above embodiments is configured to emit a stripe pattern and perform three-dimensional measurement for inspection of the printed circuit board. P1. One modified configuration may perform two-dimensional measurement, in place of or in addition to the configuration of the embodiment.

Figure 10:
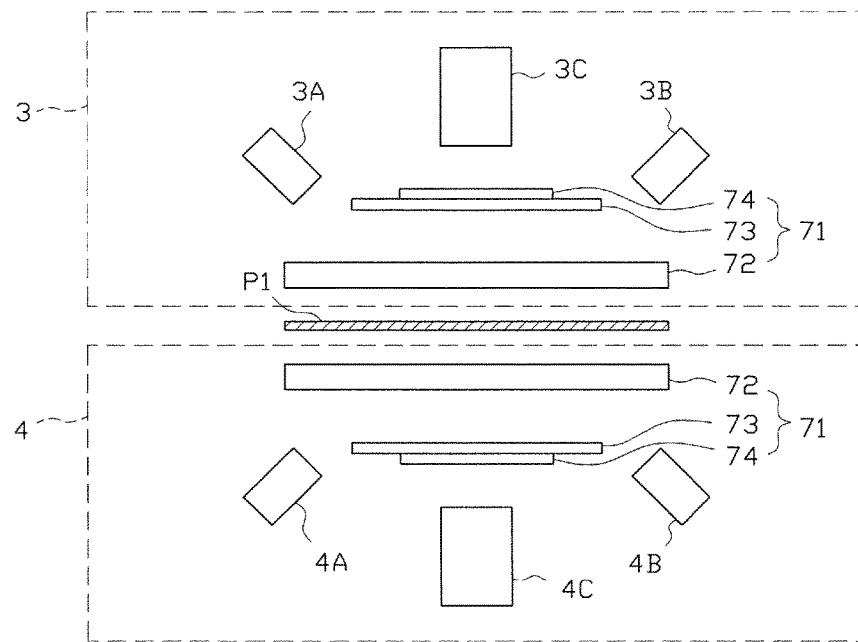
FIG. 10 is a schematic configuration diagram schematically illustrating a board inspection apparatus according to one or more embodiments of the invention.

For example, as shown in FIG. 10, the upper face inspection unit 3 may be configured to include an illumination device 71 for two-dimensional inspection, in addition to the first upper face inspection illumination device 3A, the second upper face inspection illumination device 3B and the upper face inspection camera 3C. The lower face inspection unit 4 may also be configured to include an illumination device 71 for two-dimensional measurement, in addition to the first lower face inspection illumination device 4A, the second lower face inspection illumination device 4B and the lower face inspection camera 4C.

Figure 11:
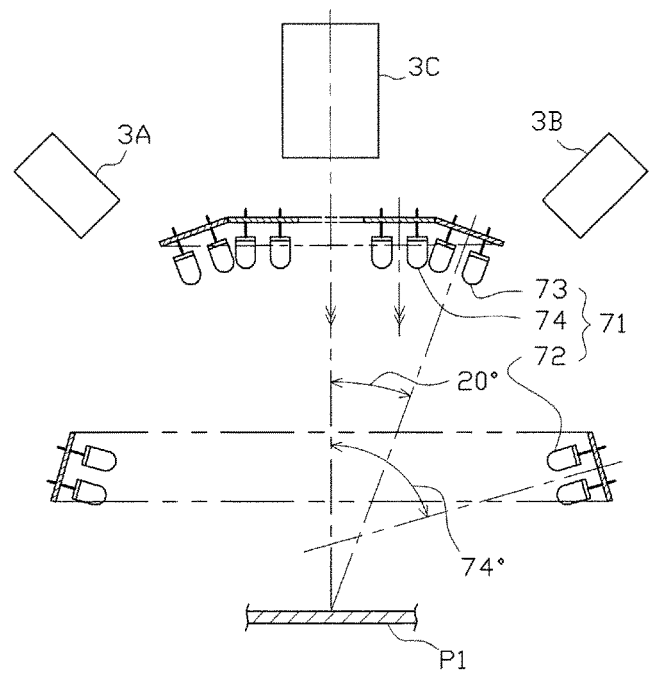
FIG. 11 is a partly enlarged sectional view illustrating an illumination device for two-dimensional inspection according to one or more embodiments of the invention.

As shown in FIGS. 10 and 11, the illumination device 71 includes a first ring light 72 located closest to the printed circuit board P1, a second ring light 73 located second closest to the printed circuit board P1 next to the first ring light 72 and a third ring light 74 located at a position most away from the printed circuit board P1.

Each of the ring lights 72 to 74 is configured to switch over emission of three monochromatic lights, i.e., red light, green light and blue light. The first ring light 72 is configured to irradiate the printed circuit board P1 with light at a large incident angle (for example, 74 degrees). The second ring light 73 is configured to irradiate the printed circuit board P1 with light at an intermediate incident angle (for example, 20 degrees). The third ring light 74 is configured to irradiate the printed circuit board P1 with light at a small incident angle (for example, 0 degree).

One modified configuration employed for inspection (image acquisition process), for example, with regard to a predetermined inspection area on the upper face side of the printed circuit board P1 may perform at least one imaging process among one imaging process with the red light emitted from all the ring lights 72 to 74, one imaging process with the blue light emitted from all the ring lights 72 to 74, one imaging process with the green light emitted from all the ring lights 72 to 74, one imaging process with the monochromatic light (for example, blue light) emitted from the first ring light 72 at a large incident angle, one imaging process with the monochromatic light (for example, green light) emitted from the second ring light 73 at an intermediate incident angle and one imaging process with the monochromatic light (for example, red light) emitted from the third ring light 74 at a small incident angle, in addition to at least either one of a plurality of imaging processes with a stripe pattern emitted from the first upper face inspection illumination device 3A and a plurality of imaging processes with a stripe pattern emitted from the second upper face inspection illumination device 3B (the same applies to inspection on the lower face side of the printed circuit board P1).

The above configuration may be modified to perform any of various two-dimensional measurements, for example, extraction of any of various areas such as solder printing area, electrode area and silk printing area, detection of any foreign substance, measurement of the area of the solder paste P4, detection of a positional misalignment or bridge detection, in addition to the three-dimensional measurement.

Another modified configuration may not perform the three-dimensional measurement but may perform only two-dimensional measurement with omission of the first upper face inspection illumination device 3A, the second upper face inspection illumination device 3B, the first lower face inspection illumination device 4A and the second lower face inspection illumination device 4B.

Each of the above embodiments is configured to perform a plurality of imaging processes in one image acquisition process with regard to a predetermined inspection area. This is, however, not essential. A modified configuration may perform only one imaging process in one image acquisition process with regard to a predetermined inspection area.

(f) The processing operations of the upper face inspection unit and the lower face inspection unit in inspection of both the upper face and the lower face of the printed circuit board P1 are not limited to the respective embodiments described above (i.e., the examples shown in FIGS. 5A to 5C). Any other configuration may be employed as long as the configuration stops emission of light on the lower face side (or on the upper face side) at least during the execution time period of an image acquisition process with regard to a predetermined inspection area on the upper face side (or on the lower face side) of the printed circuit board P1 and thereby prevents leakage of light to the upper face side (or to the lower face side).

For example, according to the above embodiments, the moving time period when each of the inspection units 3 and 4 is moved (except some part) is set to be shorter than the execution time period of one image acquisition process with regard to a predetermined inspection area by each of the inspection cameras 3C and 4C. According to another embodiment, the moving time period when each of the inspection units 3 and 4 is moved may be set to be longer than the execution time period of one image acquisition process.

In this case, for example, after termination of an image acquisition process with regard to a predetermined inspection area by the upper face inspection unit 3 (upper face inspection camera 3C), one modified configuration may start a moving process of the upper face inspection unit 3 and may also start an imaging process using the lower face inspection unit 4 (lower face inspection camera 4C). After termination of this imaging process, this modified configuration may wait for termination of the moving process of the upper face inspection unit 3 and may start a next imaging process using the upper face inspection unit 3. Another modified configuration may start a moving process of the upper face inspection unit 3 after termination of an imaging process using the upper face inspection unit 3 and may also start an imaging process using the lower face inspection unit 4 after elapse of a predetermined time period (for example, 1 msec).

Setting a relatively long time to the time period required for the moving process of each of the inspection units 3 and 4 suppresses the vibration and the like during the move of each of the inspection units 3 and 4. This results in reducing the influence of the vibration and the like on imaging and thereby improves the inspection accuracy.

(g) The processing operations of the upper face inspection unit 3 and the lower face inspection unit 4 in the image acquisition process with regard to each inspection area are not limited to each of the embodiments described above (i.e., the example shown in FIG. 4).

For example, according to the above embodiments, the data transfer (read-out) period of each of the inspection cameras 3C and 4C is set to be shorter than the execution time period of one imaging process by each of the inspection cameras 3C and 4C. According to another embodiment, the data transfer period may be set to be longer than the execution time period of one imaging process.

In this case, for example, one modified configuration may start data transfer by the upper face inspection camera 3C after termination of an imaging process using the upper face inspection camera 3C and may also start an imaging process using the lower face inspection camera 4C. After termination of this imaging process using the lower face inspection camera 4C, the modified configuration may wait for termination of a data transfer period by the upper face inspection camera 3C (i.e., a time period in which an imaging process is not allowed to be performed) and start a next imaging process using the upper face inspection camera 3C. Another modified configuration may start data transfer by the upper face inspection camera 3C after termination of an imaging process using the upper face inspection camera 3C and may start an imaging process using the lower face inspection camera 4C after elapse of a predetermined time period (for example, 1 msec).

In any of these modified configurations, the operating and control processes of the respective grid plates such as the grid plate 3Ab are naturally performed according to the imaging processes using the respective inspection cameras 3C and 4C. In other words, the grid plate should be stopped to stand by when there is a time lag.

(h) According to each of the above embodiments, a CCD sensor is employed as the imaging element of each of the inspection cameras 3C and 4C. This imaging element is, however, not essential, but another imaging element such as CMOS sensor may be employed.

A configuration using a conventional CCD sensor or the like is not allowed to perform a next imaging (exposure) process during data transfer. Accordingly the imaging process and the data transfer process are to be alternately repeated when a plurality of imaging processes are required.

A configuration using a CMOS sensor or a CCD sensor having the function of allowing for exposure during data transfer, on the other hand, allows the imaging process and the data transfer process to be performed in a partly overlapped manner.

When the data transfer period is set longer than the execution time period of one imaging process as described above, for example, the latter configuration may start data transfer by the upper face inspection camera 3C after termination of an imaging process using the upper face inspection camera 3C and may also start an imaging process using the lower face inspection camera 4C. Without waiting for termination of a data transfer period by the upper face inspection camera 3C, this configuration may start a next imaging process using the upper face inspection camera 3C, simultaneously with termination of the imaging process using the lower face inspection camera 4C.

Figure 12:
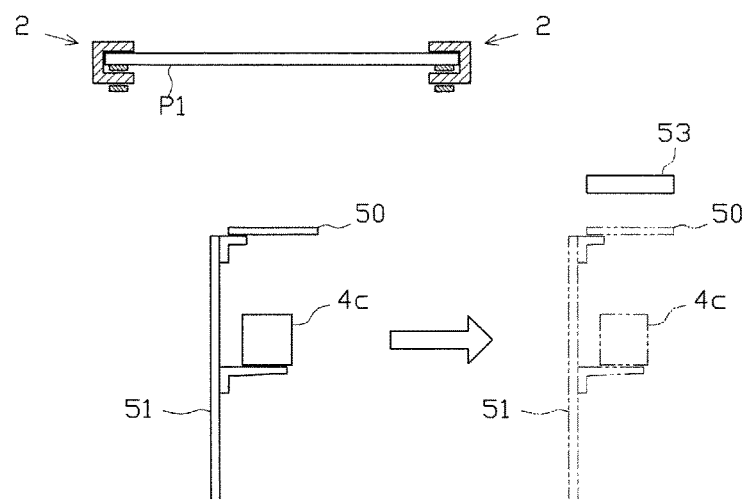
FIG. 12 is a schematic configuration diagram schematically illustrating a protective cover for a lower face inspection camera and its inspection mechanism according to one or more embodiments of the invention.

(i) Although not being specifically referred to in the each of the above embodiments, for example, the lower face inspection camera 4C located below the conveying path of the printed circuit board P1 may be provided with a protective cover 50 as shown in FIG. 12.

There is a possibility that a foreign substance such as solder residue falling down from the printed circuit board P1 may adhere to the lower face inspection camera 4C located below the conveying path of the printed circuit board P1. Providing the protective cover 50 suppresses any foreign substance from adhering to the lower face inspection camera 4C.

The protective cover 50 is formed from a transparent member, and the lower inspection camera 4C is allowed to take an image of the lower face of the printed circuit board P1 across the protective cover 50.

Deposition of any dirt or adhesion of any foreign substance on the protective cover 50 is, however, likely to interfere with the inspection. Accordingly, it is also beneficial that the board inspection apparatus 1 is provided with a cover inspection mechanism configured to perform an inspection in order to determine whether any foreign substance or the like adheres to the protective cover 50. The following describes a concrete example of the cover inspection mechanism.

As shown in FIG. 12, the lower face inspection camera 4C and the protective cover 50 are integrally assembled by means of a holder 51. The lower face inspection camera 4C and the protective cover 50 together with the holder 51 are moved to a position that deviates from the position below the conveying path of the printed circuit board P1 (cover inspection position) by non-illustrated drive means during a time period after a printed circuit board P1 for which inspection has been just completed is carried out of the board inspection apparatus 1 and before a new printed circuit board P1 is carried into the board inspection apparatus 1.

A transmitted illumination device 53 is provided at the cover inspection position to be located above the protective cover 50. After the camera 4C is focused on the protective cover 50, the camera 4C serves to take an image of the transmitted light that is emitted from the transmitted illumination device 53 and is transmitted through the protective cover 50, for the purpose of inspection of foreign substance.

Figure 13:
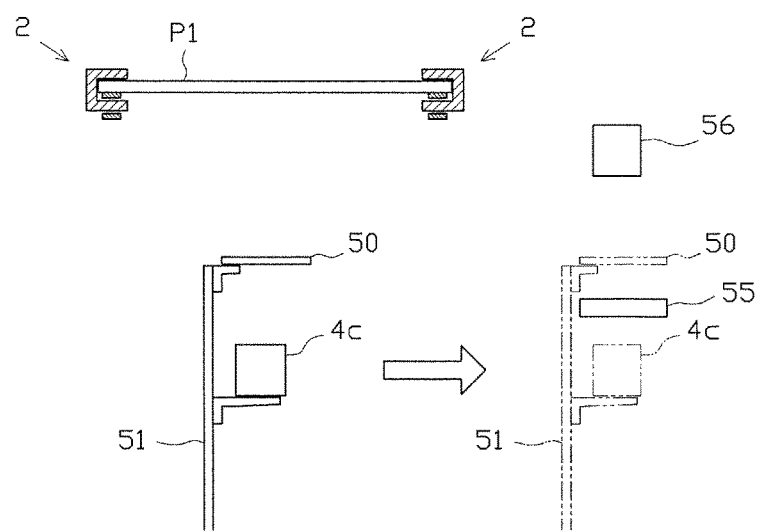
FIG. 13 is a schematic configuration diagram schematically illustrating a protective cover for the lower face inspection camera and its inspection mechanism according to one or more embodiments of the invention.

Like an example shown in FIG. 13, a transmitted illumination device 55 placed below the protective cover 50 may be provided at the cover inspection position, and a camera 56 exclusively used for inspection of the cover may be provided at a position above the protective cover 50. The camera 56 serves to take an image of the transmitted light that is emitted from the transmitted illumination device 55 and is transmitted through the protective cover 50, for the purpose of inspection of foreign substance.

Figure 14:
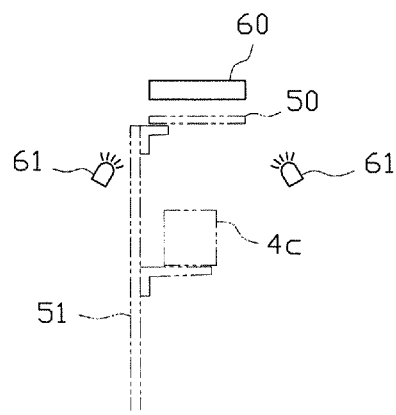
FIG. 14 is a schematic configuration diagram schematically illustrating a protective cover for the lower face inspection camera and its inspection mechanism according to one or more embodiments of the invention.

A reflected illumination device may be used, in place of the transmitted illumination device, for inspection of foreign substance. For example, as shown in FIG. 14, a blackboard 60 may be provided at the cover inspection position to be located above the protective cover 50, and a reflected illumination device 61 may be provided to irradiate the protective cover 50 with light emitted obliquely upward. After the camera 4C is focused on the protective cover 50, the camera 4C serves to take an image of the reflected light that is emitted from the reflected illumination device 61 and is reflected from the protective cover 50, for the purpose of inspection of foreign substance.

Figure 15:
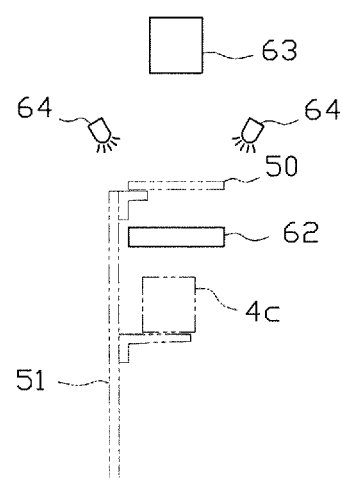
FIG. 15 is a schematic configuration diagram schematically illustrating a protective cover for the lower face inspection camera and its inspection mechanism according to one or more embodiments of the invention.

Like an example shown in FIG. 15, a blackboard 62 placed below the protective cover 50, a camera 63 located above the protective cover 50 and exclusively used for inspection of the cover, and a reflected illumination device 64 configured to irradiate the protective cover 50 with light emitted obliquely downward may be provided at the cover inspection position. The camera 63 serves to take an image of the reflected light that is emitted from the reflected illumination device 64 and is reflected from the protective cover 50, for the purpose of inspection of foreign substance.

A mechanism configured to remove the foreign substance from the protective cover 50 may be provided in addition to any of the various cover inspection mechanisms described above. When any foreign substance or the like is detected on the protective cover 50 by any of the various cover inspection mechanisms described above, a predetermined foreign substance removal mechanism may be activated to remove the foreign substance.

Examples of the foreign substance removal mechanism include a mechanism configured to spray the air and thereby blow out any foreign substance from the protective cover 50, a mechanism configured to sweep away any foreign substance by means of a brush or the like, a mechanism configured to place thin films on the protective cover 50 and successively peel off a stained thin film (tear off function), and a mechanism configured to place a film roll on the protective cover 50 and successively roll up a stained part of the film roll (roll off function).

A protective cover configured to protect the entire lower face inspection unit 4 may be provided, in place of the protective cover 50 configured to protect only the lower face inspection camera 4C. The protective cover configured to protect the entire lower face inspection unit 4 is, however, likely to provide a side inspection area in the inspection of foreign substance and increase the inspection time. This modified configuration also increases the size of the protective cover and is thereby likely to expand the size of the entire apparatus and increase the overall weight of the apparatus. From these points of view, it is also beneficial to provide the protective cover 50 configured to protect only the lower face inspection camera 4C.

(j) Each of the embodiments described above is configured to provide the first recognition mark [A] and the second recognition mark [B] on the surface side of the printed circuit board P1 and to provide the first recognition mark [a] and the second recognition mark [b] on the rear face side of the printed circuit board P1, as the specified objects for positioning.

The configuration of the specified objects, for example, the number, the shape, the size, the position and the type of the specified objects, is not limited to the above embodiments. For example, a modified configuration may provide the recognition mark at only one place or may provide the recognition mark at three or more places on both the surface and the rear face of the printed circuit board P1. A through hole formed to pass through the printed circuit board P1 between the surface and the rear face may be used as the specified object for positioning. In some cases, a through hole for the circuit may also be used as the specified object for positioning. In another example, part of the electrode pattern P3 may be used as the specified object for positioning.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST 1 board inspection apparatus, 2 conveying mechanism, 3 upper face inspection unit, 3A first upper face inspection illumination device, 3B second upper face inspection illumination device, 3C upper face inspection camera, 4 lower face inspection unit, 4A first lower face inspection illumination device, 4B second lower face inspection illumination device, 4C lower face inspection camera, 6 control device, P1 printed circuit board, P4 solder paste

What is claimed is:

1. A board inspection apparatus comprising:
   a surface-side irradiator that irradiates a surface side of each of a plurality of first inspection areas of a board;
   a surface-side camera that takes a surface-side image of the surface side irradiated by the surface-side irradiator;
   a rear face-side irradiator that irradiates a rear face side of each of a plurality of second inspection areas of the board;
   a rear face-side camera that takes a rear face-side image of the rear face side irradiated by the rear face-side irradiator; and
   a controller that:
      moves the surface-side irradiator and the surface-side camera to a position corresponding to the surface side of each of the first inspection areas;
      moves the rear face-side irradiator and the rear face-side camera to a position corresponding to the rear face side of each of the second inspection areas; and
      inspects the surface side of each of the first inspection areas and the rear face side of each of the second inspection areas based on the surface-side image and the rear face-side image, respectively, wherein
   the surface-side camera and the rear face-side camera alternately take the surface-side image and the rear face-side image,
   the surface-side camera takes the surface-side image when the rear face-side irradiator stops the irradiation, and subsequently the controller moves the surface-side irradiator and the surface-side camera to a position corresponding to a surface side of a next inspection area and the rear face-side camera takes the rear face-side image when the surface-side irradiator stops the irradiation, or
   the rear face-side camera takes the rear face-side image when the surface-side irradiator stops the irradiation, and subsequently the controller moves the rear face-side irradiator and the rear face-side camera to a position corresponding to a rear face side of a next inspection area and the surface-side camera takes the surface-side image when the rear face-side irradiator stops the irradiation,
   the plurality of first inspection areas are set in advance on an upper face of the board based on a size of an imaging range of the surface-side camera, and
   the plurality of second inspection areas are set in advance on a lower face of the board based on a size of an imaging range of the rear face-side camera.

2. The board inspection apparatus according to claim 1, wherein
   the rear face-side camera takes the rear face-side image during a moving time period of the surface-side irradiator and the surface-side camera, and
   the surface-side camera takes the surface-side image during a moving time period of the rear face-side irradiator and the rear face-side camera.

3. The board inspection apparatus according to claim 1, wherein
   the surface-side irradiator and the surface-side camera are sequentially moved to the position corresponding to the surface side of each of the first inspection areas according to a surface-side inspection sequence, and the surface-side camera sequentially takes the surface-side image of each of the first inspection areas,
   the rear face-side irradiator and the rear face-side camera are sequentially moved to the position corresponding to the rear face side of each of the second inspection areas according to a rear face-side inspection sequence, and the rear face-side camera sequentially takes the rear face-side image of each of the second inspection areas, and
   the surface-side inspection sequence is set such that a moving path of the surface-side irradiator and the surface-side camera is a shortest path from a predetermined starting point and/or the rear face-side inspection sequence is set such that a moving path of the rear face-side irradiator and the rear face-side camera is a shortest path from a predetermined starting point.

4. The board inspection apparatus according to claim 2, wherein
   the surface-side irradiator and the surface-side camera are sequentially moved to the position corresponding to the surface side of each of the first inspection areas according to a surface-side inspection sequence, and the surface-side camera sequentially takes the surface-side image of each of the first inspection areas, the rear face-side irradiator and the rear face-side camera are sequentially moved to the position corresponding to the rear face side of each of the second inspection areas according to a rear face-side inspection sequence, and the rear face-side camera sequentially takes the rear face-side image of each of the second inspection areas, and the surface-side inspection sequence is set such that a moving path of the surface-side irradiator and the surface-side camera is a shortest path from a predetermined starting point and/or the rear face-side inspection sequence is set such that a moving path of the rear face-side irradiator and the rear face-side camera is a shortest path from a predetermined starting point.

5. The board inspection apparatus according to claim 1, wherein at least one surface-side object for positioning is provided on a surface of the board, and at least one rear face-side object for positioning is provided on a rear face of the board, after imaging the at least one surface-side object, the surface-side camera sequentially takes the surface-side image of each of the first inspection areas, and after imaging the at least one rear face-side object, the rear face-side camera sequentially takes the rear face-side image of each of the second inspection areas.

6. The board inspection apparatus according to claim 2, wherein at least one surface-side object for positioning is provided on a surface of the board, and at least one rear face-side object for positioning is provided on a rear face of the board, after imaging the at least one surface-side object, the surface-side camera sequentially takes the surface-side image of each of the first inspection areas, and after imaging the at least one rear face-side object, the rear face-side camera sequentially takes the rear face-side image of each of the second inspection areas.

7. The board inspection apparatus according to claim 3, wherein at least one surface-side object for positioning is provided on a surface of the board, and at least one rear face-side object for positioning is provided on a rear face of the board, after imaging the at least one surface-side object, the surface-side camera sequentially takes the surface-side image of each of the first inspection areas, and after imaging the at least one rear face-side object, the rear face-side camera sequentially takes the rear face-side image of each of the second inspection areas.

8. The board inspection apparatus according to claim 4, wherein at least one surface-side object for positioning is provided on a surface of the board, and at least one rear face-side object for positioning is provided on a rear face of the board, after imaging the at least one surface-side object, the surface-side camera sequentially takes the surface-side image of each of the first inspection areas, and after imaging the at least one rear face-side object, the rear face-side camera sequentially takes the rear face-side image of each of the second inspection areas.

9. The board inspection apparatus according to claim 5, wherein an inspection area in a shortest distance from the surface-side object imaged last is set as an inspection area for which the surface-side camera takes the surface-side image first, and/or an inspection area in a shortest distance from the rear face-side object imaged last is set as an inspection area for which the rear face-side camera takes the rear face-side image first.

10. The board inspection apparatus according to claim 6, wherein an inspection area in a shortest distance from the surface-side object imaged last is set as an inspection area for which the surface-side camera takes the surface-side image first, and/or an inspection area in a shortest distance from the rear face-side object imaged last is set as an inspection area for which the rear face-side camera takes the rear face-side image first.

11. The board inspection apparatus according to claim 7, wherein an inspection area in a shortest distance from the surface-side object imaged last is set as an inspection area for which the surface-side camera takes the surface-side image first, and/or an inspection area in a shortest distance from the rear face-side object imaged last is set as an inspection area for which the rear face-side camera takes the rear face-side image first.

12. The board inspection apparatus according to claim 8, wherein an inspection area in a shortest distance from the surface-side object imaged last is set as an inspection area for which the surface-side camera takes the surface-side image first, and/or an inspection area in a shortest distance from the rear face-side object imaged last is set as an inspection area for which the rear face-side camera takes the rear face-side image first.

13. The board inspection apparatus according to claim 5, further comprising a memory that stores information about a relative positional relationship between the surface-side camera and the rear face-side camera obtained in advance, wherein the controller corrects a relative positional relationship between the surface-side camera and the surface of the board and a relative positional relationship between the rear face-side camera and the rear face of the board based on: position information about the imaged surface-side object; position information about the imaged rear face-side object; and the stored information about the relative positional relationship between the surface-side camera and the rear face-side camera.

14. The board inspection apparatus according to claim 6, further comprising a memory that stores information about a relative positional relationship between the surface-side camera and the rear face-side camera obtained in advance, wherein the controller corrects a relative positional relationship between the surface-side camera and the surface of the board and a relative positional relationship between the rear face-side camera and the rear face of the board based on: position information about the imaged surface-side object; position information about the imaged rear face-side object; and the stored information about the relative positional relationship between the surface-side camera and the rear face-side camera.

15. The board inspection apparatus according to claim 7, further comprising
 a memory that stores information about a relative positional relationship between the surface-side camera and the rear face-side camera obtained in advance, wherein
 the controller corrects a relative positional relationship between the surface-side camera and the surface of the board and a relative positional relationship between the rear face-side camera and the rear face of the board based on: position information about the imaged surface-side object; position information about the imaged rear face-side object; and the stored information about the relative positional relationship between the surface-side camera and the rear face-side camera.

16. The board inspection apparatus according to claim 8, further comprising
 a memory that stores information about a relative positional relationship between the surface-side camera and the rear face-side camera obtained in advance, wherein
 the controller corrects a relative positional relationship between the surface-side camera and the surface of the board and a relative positional relationship between the rear face-side camera and the rear face of the board based on: position information about the imaged surface-side object; position information about the imaged rear face-side object; and the stored information about the relative positional relationship between the surface-side camera and the rear face-side camera.

17. The board inspection apparatus according to claim 1, wherein
 at least one of the surface-side irradiator and the rear face-side irradiator emits patterned light having a light intensity distribution of a stripe shape, and
 the controller performs three-dimensional measurement by a phase shift method, based on a plurality of images taken with the patterned light of different phases.

18. The board inspection apparatus according to claim 2, wherein
 at least one of the surface-side irradiator and the rear face-side irradiator emits patterned light having a light intensity distribution of a stripe shape, and
 the controller performs three-dimensional measurement by a phase shift method, based on a plurality of images taken with the patterned light of different phases.

19. The board inspection apparatus according to claim 3, wherein
 at least one of the surface-side irradiator and the rear face-side irradiator emits patterned light having a light intensity distribution of a stripe shape, and
 the controller performs three-dimensional measurement by a phase shift method, based on a plurality of images taken with the patterned light of different phases.

20. The board inspection apparatus according to claim 1, wherein
 the board is either a printed circuit board on which solder paste is printed or a wafer substrate on which a solder bump is formed.

* * * * *